United States Patent [19]

Motojima et al.

[11] Patent Number: 4,866,201
[45] Date of Patent: Sep. 12, 1989

[54] CYCLOHEXANE DERIVATIVES HAVING PLANT-GROWTH REGULATING ACTIVITIES AND USES OF THESE DERIVATIVES

[75] Inventors: Kenji Motojima, Kakegawa; Takeshige Miyazawa, Shizuoka; Yasufumi Toyokawa, Shizuoka; Masafumi Matsuzawa, Shizuoka; Hiroshi Hokari, Shizuoka; Shoji Kusano, Shizuoka, all of Japan

[73] Assignee: Kumiai Chemical Industry Co., Ltd., Japan

[21] Appl. No.: 70,712

[22] Filed: Jul. 7, 1987

Related U.S. Application Data

[62] Division of Ser. No. 761,497, Aug. 1, 1985, Pat. No. 4,678,496, which is a division of Ser. No. 534,827, Sep. 22, 1983, Pat. No. 4,560,403.

[30] Foreign Application Priority Data

Apr. 22, 1983 [JP] Japan .................................. 58-71264

[51] Int. Cl.⁴ .......................................... C07C 69/757
[52] U.S. Cl. ...................................... 560/126; 549/79; 560/51; 560/53
[58] Field of Search ........................... 560/126, 51, 53; 549/79

[56] References Cited

U.S. PATENT DOCUMENTS

| | | | |
|---|---|---|---|
| 3,950,420 | 4/1976 | Sawaki | 71/106 |
| 3,989,737 | 11/1976 | Sawaki | 71/106 |
| 4,440,566 | 4/1984 | Luo | 71/106 |
| 4,517,013 | 5/1985 | Becker | 71/106 |
| 4,568,383 | 2/1986 | Jahn | 71/106 |
| 4,717,418 | 1/1988 | Warner | 71/106 |
| 4,740,237 | 4/1988 | Jahn | 71/106 |

FOREIGN PATENT DOCUMENTS 54-63052 5/1979 Japan .
58-164543 9/1983 Japan .

Primary Examiner—Michael L. Shippen
Attorney, Agent, or Firm—Lalos & Keegan

[57] ABSTRACT

A new compound is provided by a cyclohexane derivative of the formula

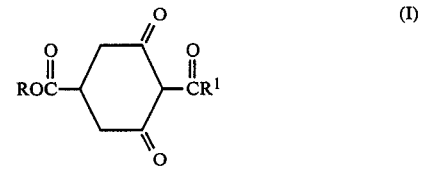

(I)

wherein R represents a hydrogen atom or an alkyl group, an alkylthioalkyl group or an unsubstituted or substituted phenyl group; and $R^1$ represents an alkyl group, an unsubstituted or substituted benzyl group, a phenethyl group, a phenoxymethyl group, a 2-thienylmethyl group, an alkoxymethyl group or an alkylthiomethyl group, or a salt of said cyclohexane compound.

This cyclohexane compound exhibits useful plant-growth regulating effects on crop-plants and also non-crop plants such as lawn and may be prepared by cyclization of an acetonylsuccinic acid dialkyl ester, followed by reaction with an organic acid chloride and by intermolecular rearrangement.

6 Claims, 7 Drawing Sheets

CYCLOHEXANE DERIVATIVES HAVING PLANT-GROWTH REGULATING ACTIVITIES AND USES OF THESE DERIVATIVES

This is a divisional of co-pending application Ser. No. 761,497 filed on Aug. 1, 1985, now U.S. Pat. No. 4,678,496 which is a division of Ser. No. 534,827 filed Sept. 22, 1983, now U.S. Pat. No. 4,560,403.

FIELD OF THE INVENTION

This invention relates to a new cyclohexane derivative, more particularly new derivative of 3,5-dioxocyclohexanecarboxylic acid, having high plant-growth regulating activities and to process for the preparation of said cyclohexane derivatives. This invention also relates to a plant-growth regulating composition comprising said cyclohexane derivative as the active ingredient, and further to a method of regulating the growth of a plant using said cyclohexane derivative.

BACKGROUND OF THE INVENTION

Various chemical compounds have been used for regulation of the growth of plants with a chemical substance, so called for the purpose of "chemical control" of the plant-growth. For example, maleic hydrazide (MH), N,N-dimethylaminosuccinic amide(known as Daminozide or B-Nine) and 2-chloroethyl trimethyl ammonium chloride (known as Chlormequat or CCC) have been employed for retardation of plant-growth, for control of emergence of sideshooting or for prevention of lodging of plants. These known compounds, however, have various drawbacks that their uses are restricted in respect of the locus, plants and time which can effectively be treated with them, that their plant-growth regulating effects are insufficient or unstable, that they are phytotoxic, and/or that they are too expensive.

We have made extensive studies in an attempt to provide new plant-growth regulators which are free from the aforementioned drawbacks of the known plant-growth regulators. As a result, we have now found that certain new cyclohexane derivatives which we have now newly synthetized exhibit some remarkable plant-growth regulating effects and are free from the drawbacks as described above.

DETAILED DESCRIPTION OF THE INVENTION

Figure 1:
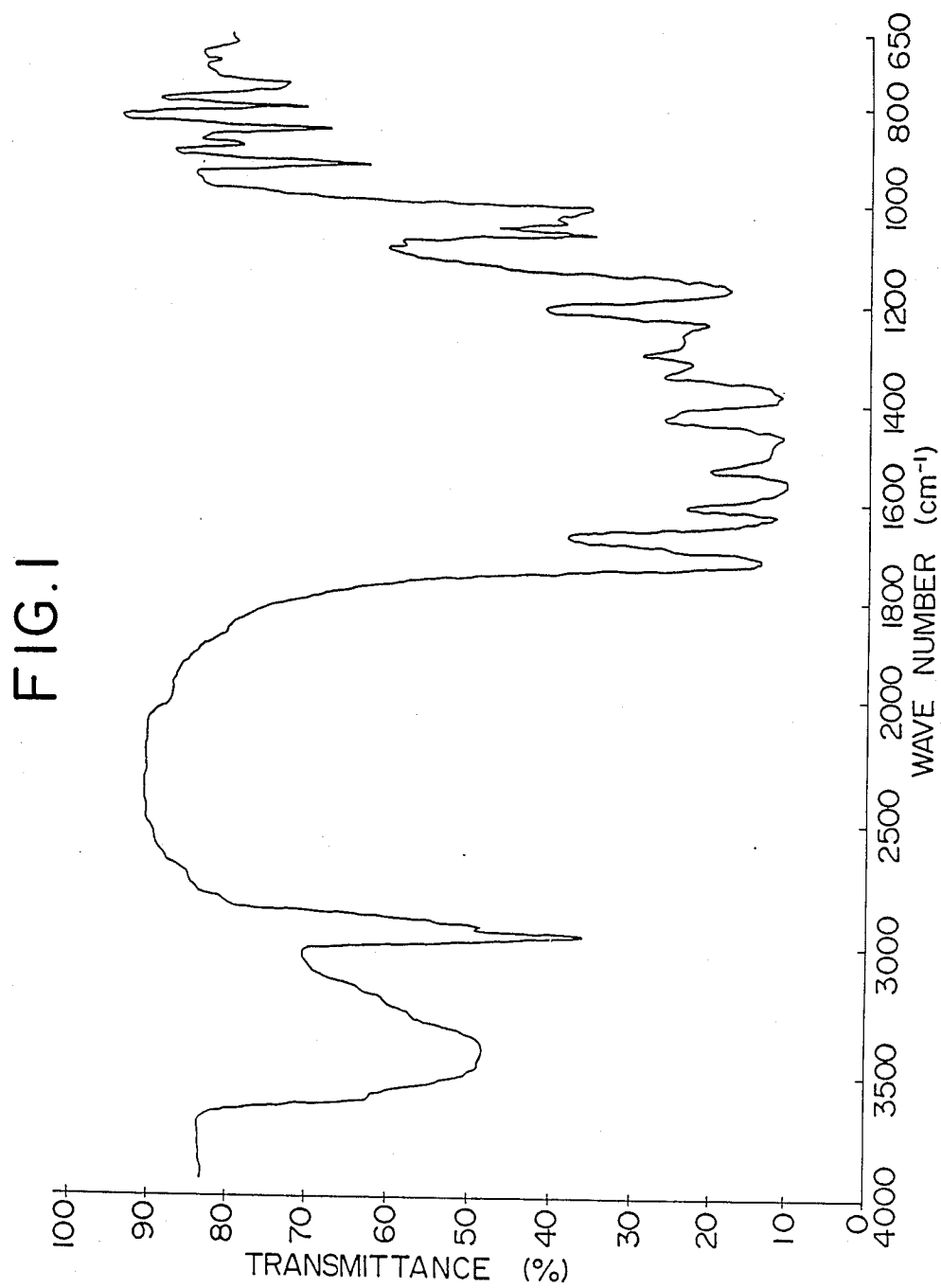

According to an aspect of this invention, therefore, there is provided a cyclohexane compound of the general formula:

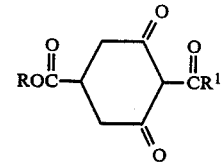

wherein R represents a hydrogen atom or an alkyl group, an alkylthioalkyl group or an unsubstituted or substituted phenyl group; and $R^1$ represents an alkyl group, an unsubstituted or substituted benzyl group, a phenethyl group, a phenoxymethyl group, a 2-thienylmethyl group, an alkoxymethyl group or an alkylthiomethyl group, or a salt of said cyclohexane compound.

The alkyl group which R may represent in the general formula (I) includes those containing 1 to 8 carbon atoms, for example, methyl, ethyl, n-propyl, iso-propyl, n-butyl, iso-butyl, sec-butyl, tert-butyl, n-pentyl, and iso-pentyl groups.

The alkyl group which $R^1$ may represent includes those of 1 to 8 carbon atoms, such as methyl, ethyl, n-propyl, iso-propyl, n-butyl, iso-butyl, n-pentyl, n-hexyl, n-heptyl and n-octyl groups.

The substituent on the substituted phenyl group which R may represent, as well as the substituent on the substituted benzyl group which $R^1$ may represent may be a lower alkyl group of 1 to 4 carbon atoms such as methyl; halo group such as chloro; and a lower alkoxyl group of 1 to 4 carbon atoms such as methoxy.

Typical examples of the cyclohexane compounds of the general formula (I) are listed in Table 1 below, where the physical properties of each compound are also indicated.

TABLE 1

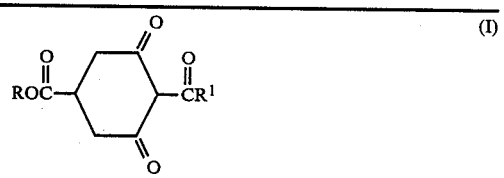

| Compound No. | R | $R^1$ | Physical Properties |
|---|---|---|---|
| 1 | $C_2H_5-$ | $CH_3-$ | m.p. 40°~42° C. |
| 2 | $n-C_3H_7-$ | " | m.p. 43°~44° C. |
| 3 | $i-C_3H_7-$ | " | m.p. 98°~100° C. |
| 4 | $n-C_4H_9-$ | " | $n_D^{20} = 1.4991$ |
| 5 | $i-C_4H_9-$ | " | m.p. 39°~40° C. |
| 6 | $s-C_4H_9-$ | " | m.p. 36°~37° C. |
| 7 | $t-C_4H_9-$ | $CH_3-$ | m.p. 76°~77° C. |
| 8 | $CH_3-$ | $C_2H_5-$ | m.p. 49°~50° C. |
| 9 | $C_2H_5-$ | " | m.p. 55°~56° C. |
| 10 | $n-C_3H_7-$ | " | $n_D^{20} = 1.4960$ |
| 11 | $i-C_3H_7-$ | " | m.p. 55°~56° C. |
| 12 | H— | " | m.p. 98°~99° C. |
| 13 | " | $n-C_3H_7-$ | m.p. 116°~119° C. |
| 14 | $CH_3-$ | " | $n_D^{20} = 1.5025$ |
| 15 | $C_2H_5-$ | " | m.p. 34°~35° C. |
| 16 | $n-C_3H_7-$ | " | $n_D^{20} = 1.5010$ |
| 17 | $i-C_3H_7-$ | " | $n_D^{20} = 1.4941$ |

TABLE 1-continued $$\text{(I)}$$

ROC(=O)—[cyclohexane-2,4-dione]—C(=O)R¹

| Compound No. | R | R¹ | Physical Properties |
|---|---|---|---|
| 18 | n-C₄H₉— | " | $n_D^{20} = 1.4930$ |
| 19 | i-C₄H₉— | " | $n_D^{20} = 1.4958$ |
| 20 | s-C₄H₉— | " | $n_D^{20} = 1.4893$ |
| 21 | i-C₅H₁₁— | " | $n_D^{20} = 1.4885$ |
| 22 | C₆H₅— | " | m.p. 91°~92° C. |
| 23 | 4-CH₃-C₆H₄— | " | m.p. 123°~124° C. |
| 24 | 4-Cl-C₆H₄— | " | m.p. 115°~116° C. |
| 25 | C₂H₅— | i-C₃H₇— | $n_D^{20} = 1.4898$ |
| 26 | " | n-C₄H₉— | $n_D^{20} = 1.4943$ |
| 27 | " | i-C₄H₉— | $n_D^{20} = 1.4948$ |
| 28 | " | n-C₅H₁₁— | $n_D^{20} = 1.4878$ |
| 29 | " | n-C₆H₁₃— | $n_D^{20} = 1.4803$ |
| 30 | " | n-C₇H₁₅— | $n_D^{20} = 1.4773$ |
| 31 | " | n-C₈H₁₇— | $n_D^{20} = 1.4650$ |
| 32 | C₂H₅— | C₆H₅-CH₂— | m.p. 67°~68° C. |
| 33 | " | C₆H₅-C₂H₄— | m.p. 80°~81° C. |
| 34 | " | C₆H₅-OCH₂— | m.p. 66°~68° C. |
| 35 | " | C₂H₅OCH₂— | $n_D^{20} = 1.5035$ |
| 36 | " | C₂H₅SCH₂— | $n_D^{20} = 1.5357$ |
| 37 | H— | CH₃— | m.p. 139°~141° C. |
| 38 | CH₃— | " | m.p. 77°~77.5° C. |
| 39 | t-C₄H₉— | C₂H₅— | m.p. 67°~69° C. |
| 40 | CH₃SC₂H₄— | n-C₃H₇— | $n_D^{20} = 1.5170$ |
| 41 | C₂H₅— | —CH₂-C₆H₄-OCH₃ (4-) | m.p. 74°~75° C. |
| 42 | " | —CH₂-C₆H₄-Cl (4-) | m.p. 78°~79° C. |

TABLE 1-continued

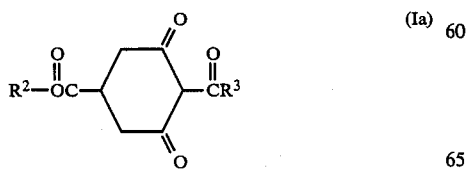
(I)

| Compound No. | R | R[1] | Physical Properties |
|---|---|---|---|
| 43 | " | -CH₂-(2-chlorophenyl) | $n_D^{20} = 1.5610$ |
| 44 | " | -CH₂-(2-thienyl) | m.p. 61°~63° C. |

Amongst the particular compounds of Table 1, the following compounds are preferred in this invention.

(1) Compound No. 8: 3,5-dioxo-4-propionylcyclohexanecarboxylic acid methyl ester;
(2) Compound No. 9: 3,5-dioxo-4-propionylcyclohexanecarboxylic acid ethyl ester;
(3) Compound No. 10: 3,5-dioxo-4-propionylcyclohexanecarboxylic acid n-propyl ester;
(4) Compound No. 13: 3,5-dioxo-4-butyrylcyclohexanecarboxylic acid;
(5) Compound No. 15: 3,5-dioxo-4-butyrylcyclohexanecarboxylic acid ethyl ester;
(6) Compound No.16: 3,5-dioxo-4-butyrylcyclohexanecarboxylic acid n-propyl ester;
(7) Compound No.17: 3,5-dioxo-4-butyrylcyclohexanecarboxylic acid isopropyl ester;
(8) Compound No.18: 3,5-dioxo-4-butyrylcyclohexanecarboxylic acid n-butyl ester;
(9) Compound No.21: 3,5-dioxo-4-butyrylcyclohexanecarboxylic acid isopentyl ester;
(10) Compound No.25: 3,5-dioxo-4-isobutyrylcyclohexanecarboxylic acid ethyl ester; and
(11) Compound No.37: 3,5-dioxo-4-acetylcyclohexanecarboxylic acid.

For plant-growth regulators to be applied onto grass swards, it is usually required that they should have a particularly improved saftety in their stimulus for human's skin and eye since they are frequently used for treatment of swards planted in golf links, parks or yards so that they are likely to be brought into direct contact with human bodies.

Through our further studies, we have found that such a class of the new cyclohexane derivative of the general formula (I) which is represented by the following general formula (Ia)

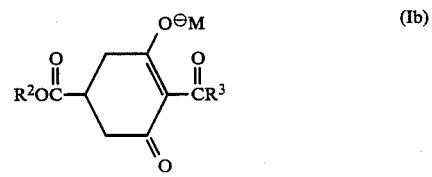
(Ia)

wherein R² represents a hydrogen atom or an alkyl group and R³ represents an alkyl group can provide such a salt with an inorganic or organic cation which exhibits a significantly reduced stimulus to skin and eye of the animal or human, as compared to the similar salt of the another classes of the new cyclohexane derivative according to the general formula (I), with retaining their excellent plant-growth regulating effects.

According to a preferred embodiment of the first aspect of this invention, therefore, there is provided a salt of a cyclohexane compound of the general formula:

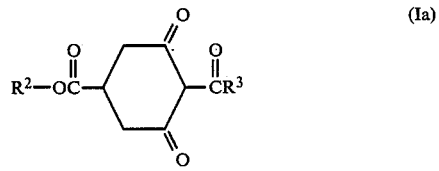
(Ia)

wherein R² represents a hydrogen atom or an alkyl group and R³ represents an alkyl group.

The salt of the new cyclohexane compound according to the general formula (Ia) may be any of the following three types:

(i) A salt of the cyclohexane compound represented by the general formula:

(Ib)

wherein R² and R³ are as defined above and M represents an organic or inorganic cation.

(ii) A salt of the cyclohexane compound represented by the general formula:

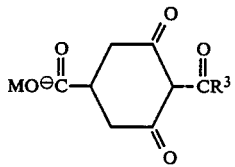

(Ic)

wherein $R^3$ and M are as defined above.

(iii) A salt of the cyclohexane compound represented by the general formula:

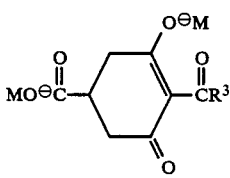

(Id)

wherein $R^3$ and M are as defined above.

In the above formulae (Ia), (Ib), (Ic) and (Id), $R^2$ is as defined hereinbefore and preferably is a hydrogen atom or an alkyl group such as methyl, ethyl, n-propyl, iso-propyl, n-butyl or iso-butyl, $R^3$ is as defined hereinbefore and preferably is an alkyl group such as mentioned just above, and M stands for an organic or inorganic cation. The inorganic cation here may be the cation of an alkali metal (including ammonium cation), an alkaline earth metal, aluminium, copper, nickel, manganese, cobalt, zinc, iron and silver. The organic cation may be a substituted ammonium ion represented by the formula:

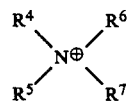

wherein $R^4$, $R^5$, $R^6$ and $R^7$ each represents a hydrogen atom or an alkyl, a hydroxyalkyl, an alkenyl, benzyl, a halogen-substituted benzyl, pyridyl or an alkyl-substituted pyridyl group, or $R^4$ and $R^5$ taken together form a polymethylene group which may optionally be interrupted by an oxygen atom.

Typical examples of the various salts of the formula (Ib), (Ic) or (Id) according to this invention are shown in Tables 2-4 below.

TABLE 2

(Ib)

| Compound No. | $R^2$ | $R^3$ | M | Physical Properties |
|---|---|---|---|---|
| 45 | $CH_3$ | $CH_3$ | $H_2N^\oplus(C_2H_4OH)_2$ | m.p. 88°~91° C. |
| 46 | " | $C_2H_5$ | " | m.p. 85°~86° C. |
| 47 | " | " | $H_2N^\oplus(CH_2\underset{\underset{OH}{\|}}{C}HCH_3)_2$ | m.p. 90°~92° C. |
| 48 | " | $n-C_3H_7$ | $H_2N^\oplus(C_2H_4OH)_2$ | m.p. 62°~64° C. |
| 49 | $C_2H_5$ | $CH_3$ | " | (see Table 5 given later) |
| 50 | " | " | $H_2N^\oplus(C_2H_5)_2$ | (see Table 5) |
| 51 | " | $C_2H_5$ | " | (see Table 5) |
| 52 | $C_2H_5$ | $C_2H_5$ | $H_2N^\oplus(n-C_3H_7)_2$ | m.p. 76°~80.5° C. |
| 53 | " | " | $H_2N^\oplus(i-C_3H_7)_2$ | m.p. 42°~44.5° C. |
| 54 | " | " | $H_2N^\oplus(C_2H_4OH)_2$ | m.p. 76°~78° C. (see Table 5) |
| 55 | " | " | $H_2N^\oplus(CH_2\underset{\underset{OH}{\|}}{C}HCH_3)_2$ | m.p. 91°~94° C. |
| 56 | " | " | $H_2N^\oplus(CH_2CH=CH_2)_2$ | (see Table 5) |
| 57 | " | " | $H_2N^\oplus(n-C_4H_9)_2$ | m.p. 94°~96° C. |
| 58 | " | " | $H_2N^\oplus(i-C_4H_9)_2$ | (see Table 5) |
| 59 | " | " | $H_2N^\oplus(CH_2\underset{\underset{(CH_2)_3}{\|}}{C}H-C_2H_5)_2$ where chain is $(CH_2)_3-CH_3$ | refractive index $n_D^{25} = 1.4965$ |
| 60 | " | " | $H_2N^\oplus(n-C_{12}H_{25})_2$ | m.p. 62°~63° C. |
| 61 | " | " | $n-C_4H_9\diagdown N^\oplus H_2 \diagup C_2H_5$ | m.p. 63°~65° C. |
| 62 | " | " | $H_3N^\oplus(t-C_4H_9)$ | refractive index |

TABLE 2-continued (Ib)

$$R^2OC(=O)-\text{cyclohexenone with } O^{\ominus}M, COR^3$$

Figure 2:
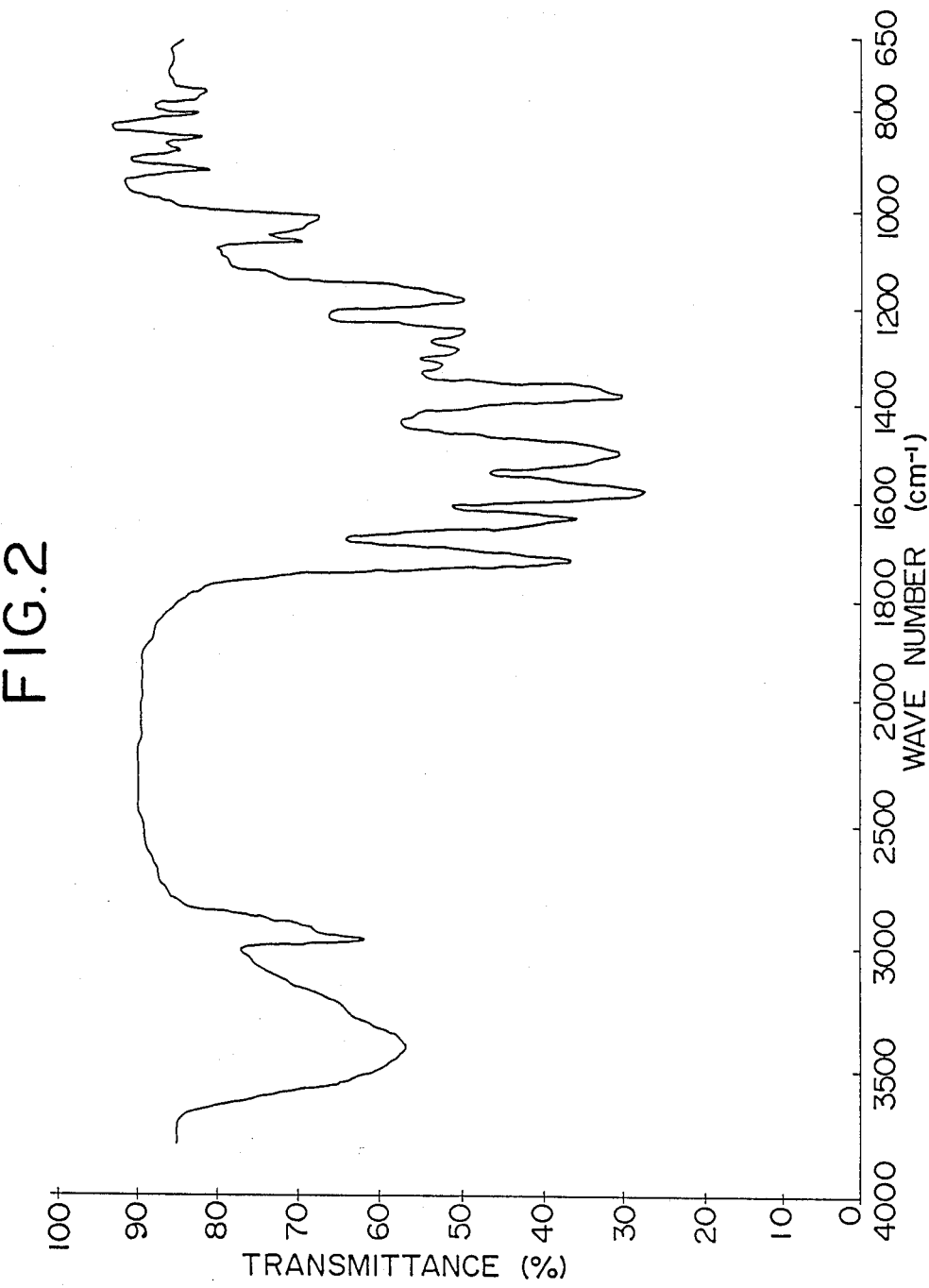
Figure 3:
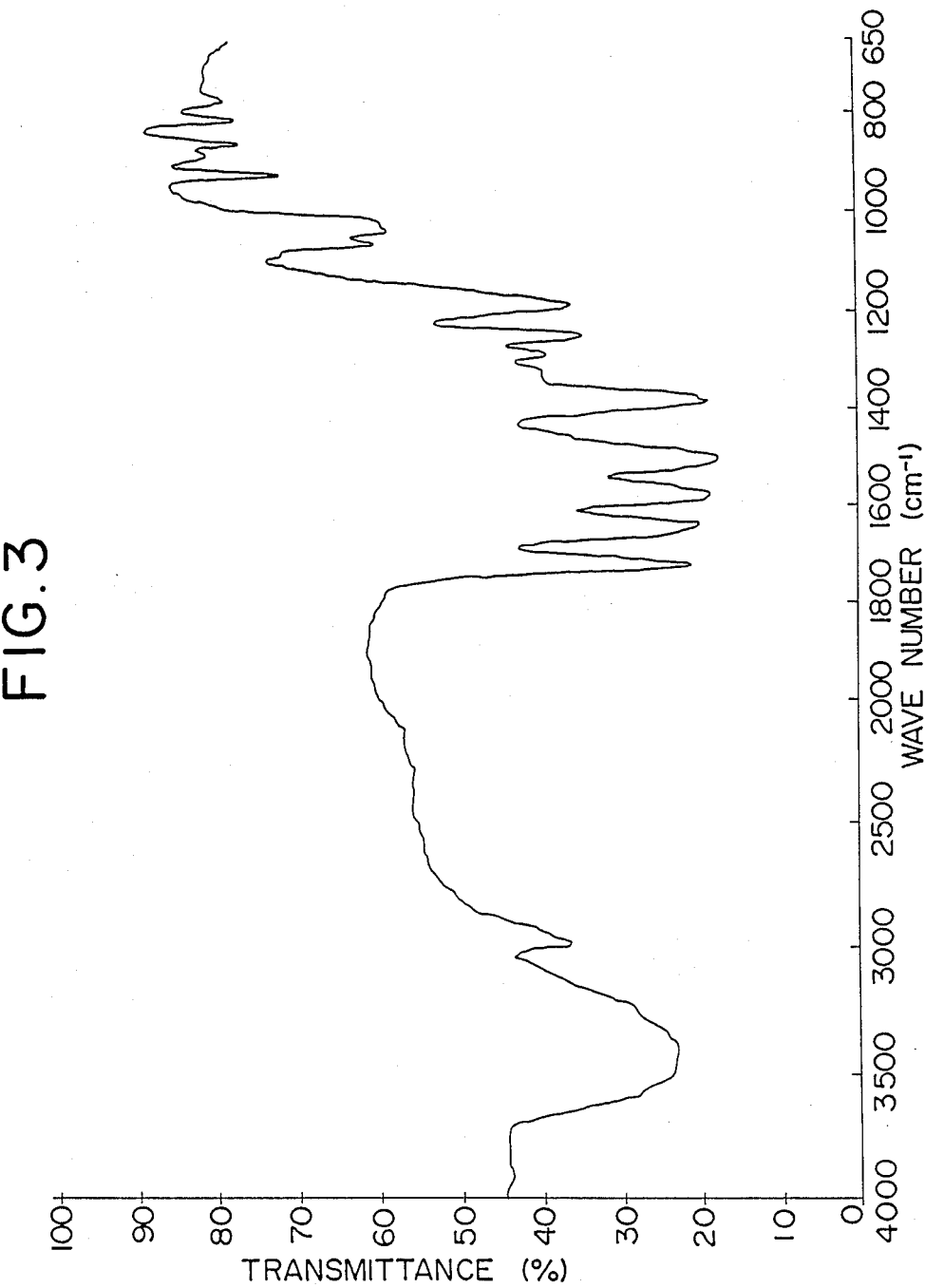
Figure 4:
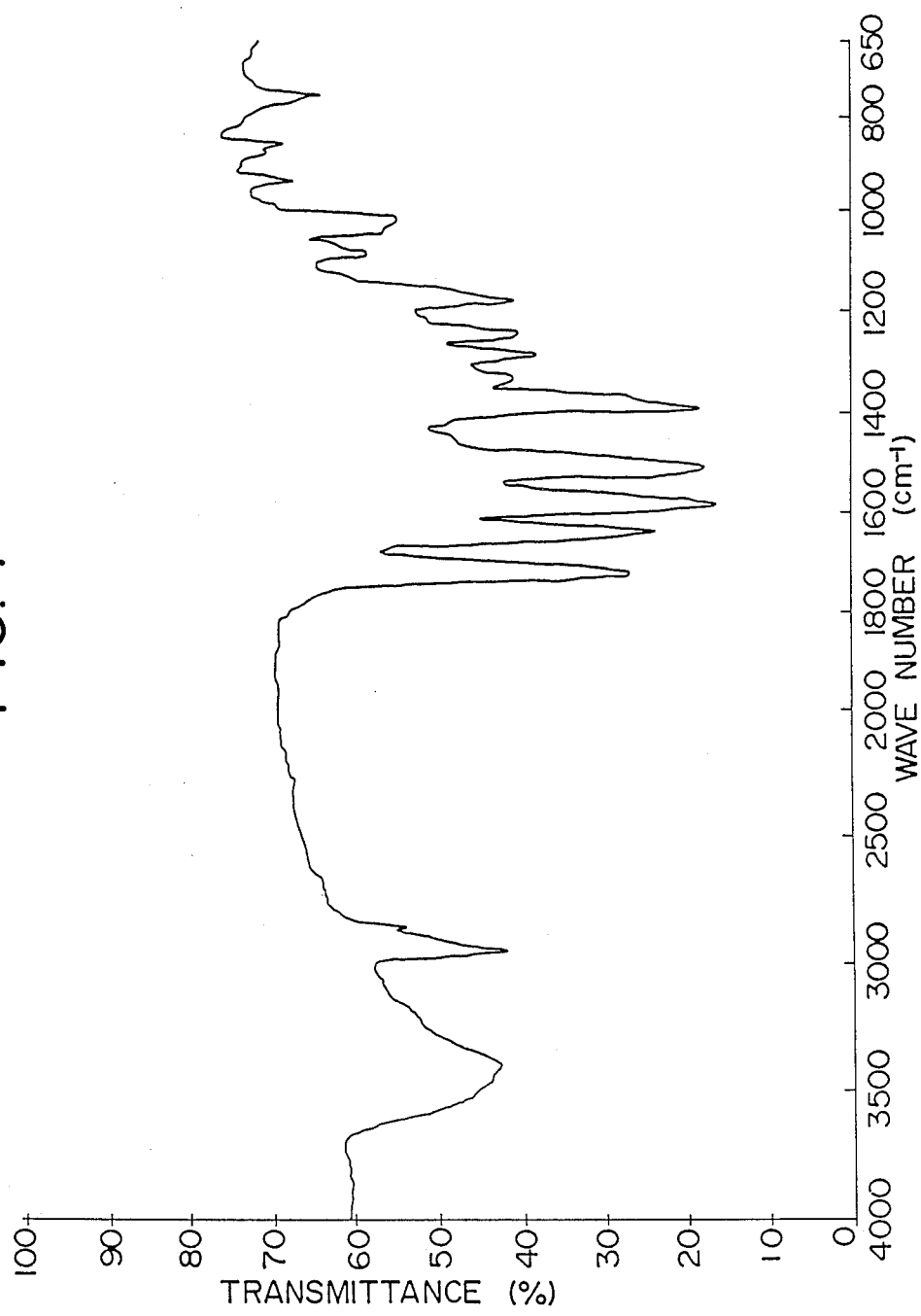
Figure 5:
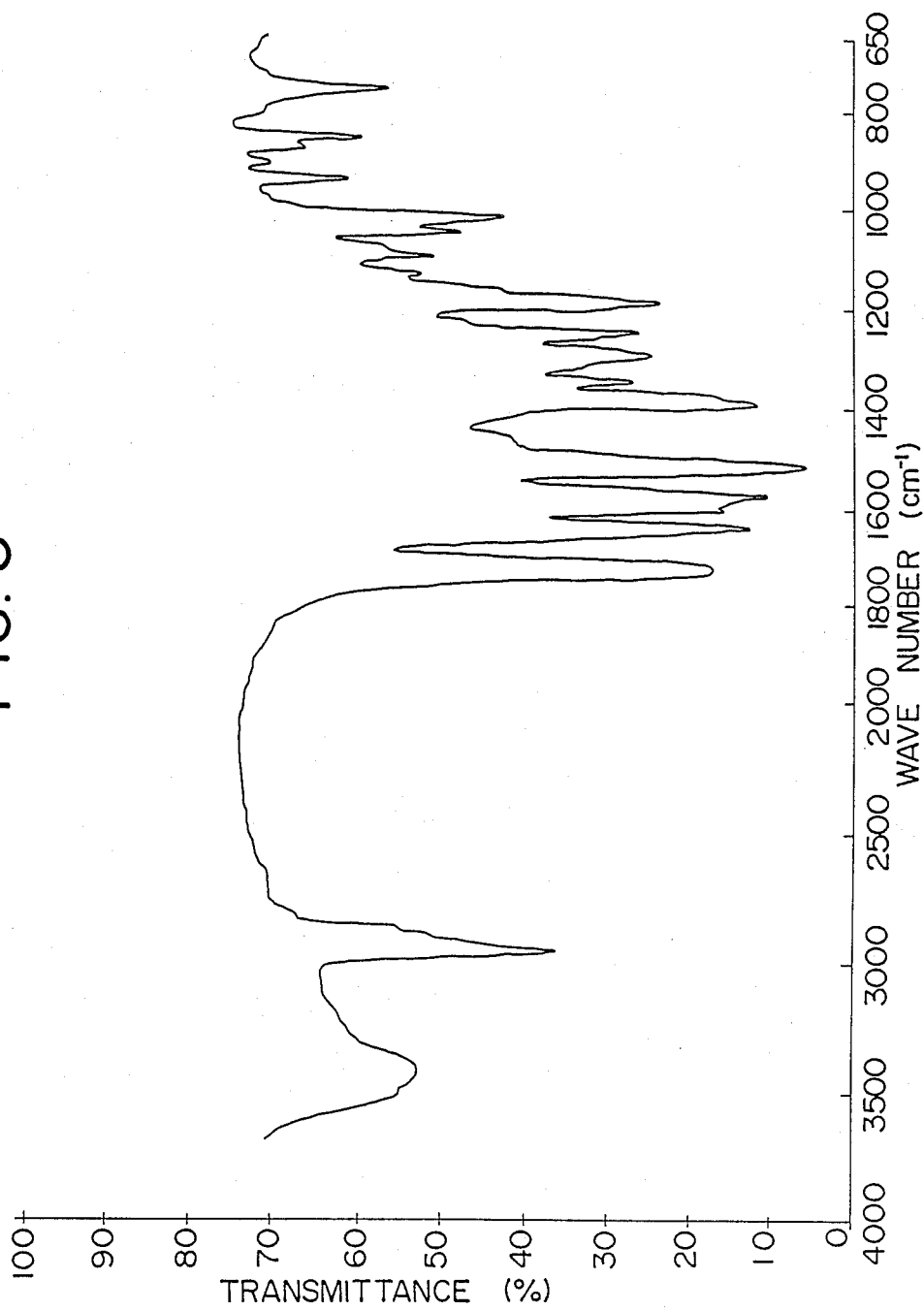

| Compound No. | $R^2$ | $R^3$ | M | Physical Properties |
|---|---|---|---|---|
| 63 | " | " | $HN^{\oplus}(C_2H_5)_3$ | $n_D^{20} = 1.5069$ refractive index $n_D^{25} = 1.5098$ |
| 64 | " | " | $HN^{\oplus}(C_2H_4OH)_3$ | m.p. 53°~56° C. |
| 65 | " | " | $H_2^{\oplus}N$—(pyrrolidine) | refractive index $n_D^{25} = 1.5505$ |
| 66 | " | " | $H_2^{\oplus}N$—(piperidine) | m.p. 55°~56° C. |
| 67 | " | " | $H_2^{\oplus}N$—(morpholine) | m.p. 55°~57° C. |
| 68 | " | " | $H_3N^{\oplus}$—(2-pyridyl) | m.p. 75°~76° C. |
| 69 | $C_2H_5$ | $C_2H_5$ | $H_3N^{\oplus}$—(3-methyl-2-pyridyl) | m.p. 67°~68° C. |
| 70 | " | " | $\frac{1}{2}Mg^{2\oplus}$ | m.p. 184°~188° C. |
| 71 | " | " | $\frac{1}{2}Cu^{2\oplus}$ | m.p. 203°~206° C. (decomp.) |
| 72 | " | " | $\frac{1}{2}Ni^{2\oplus}$ | m.p. > 290° C. |
| 73 | " | " | $\frac{1}{2}Ca^{2\oplus}$ | (see FIG. 1) |
| 74 | " | " | $Na^{\oplus}$ | (see FIG. 2) |
| 75 | " | " | $K^{\oplus}$ | (see FIG. 3) |
| 76 | " | n-$C_3H_7$ | $H_2N^{\oplus}(C_2H_5)_2$ | m.p. 63°~65° C. |
| 77 | " | " | $H_2N^{\oplus}(C_2H_4OH)_2$ | m.p. 51°~53° C. |
| 78 | " | " | $Na^{\oplus}$ | (see FIG. 4) |
| 79 | " | " | $K^{\oplus}$ | (see FIG. 5) |
| 80 | " | " | $\frac{1}{2}Ca^{2\oplus}$ | m.p. 157°~159° C. |
| 81 | " | " | $\frac{1}{3}Fe^{3\oplus}$ | refractive index $n_D^{20} = 1.5475$ |
| 82 | " | " | $\frac{1}{3}Al^{3\oplus}$ | refractive index $n_D^{20} = 1.5294$ |
| 83 | i-$C_3H_7$ | $C_2H_5$ | $H_2N^{\oplus}(C_2H_4OH)_2$ | m.p. 71°~73° C. |

TABLE 3

(Ic)

$$M^{\ominus}OC(=O)-\text{cyclohexanedione-}CR^3(=O)$$

| Compound No. | $R^3$ | M | Physical Properties |
|---|---|---|---|
| 84 | n-$C_3H_7$ | $HN^{\oplus}(C_2H_5)_3$ | refractive index |

TABLE 3-continued

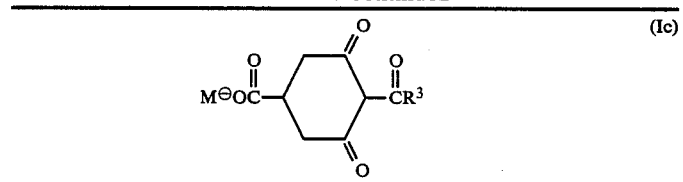

(Ic)

Figure 6:
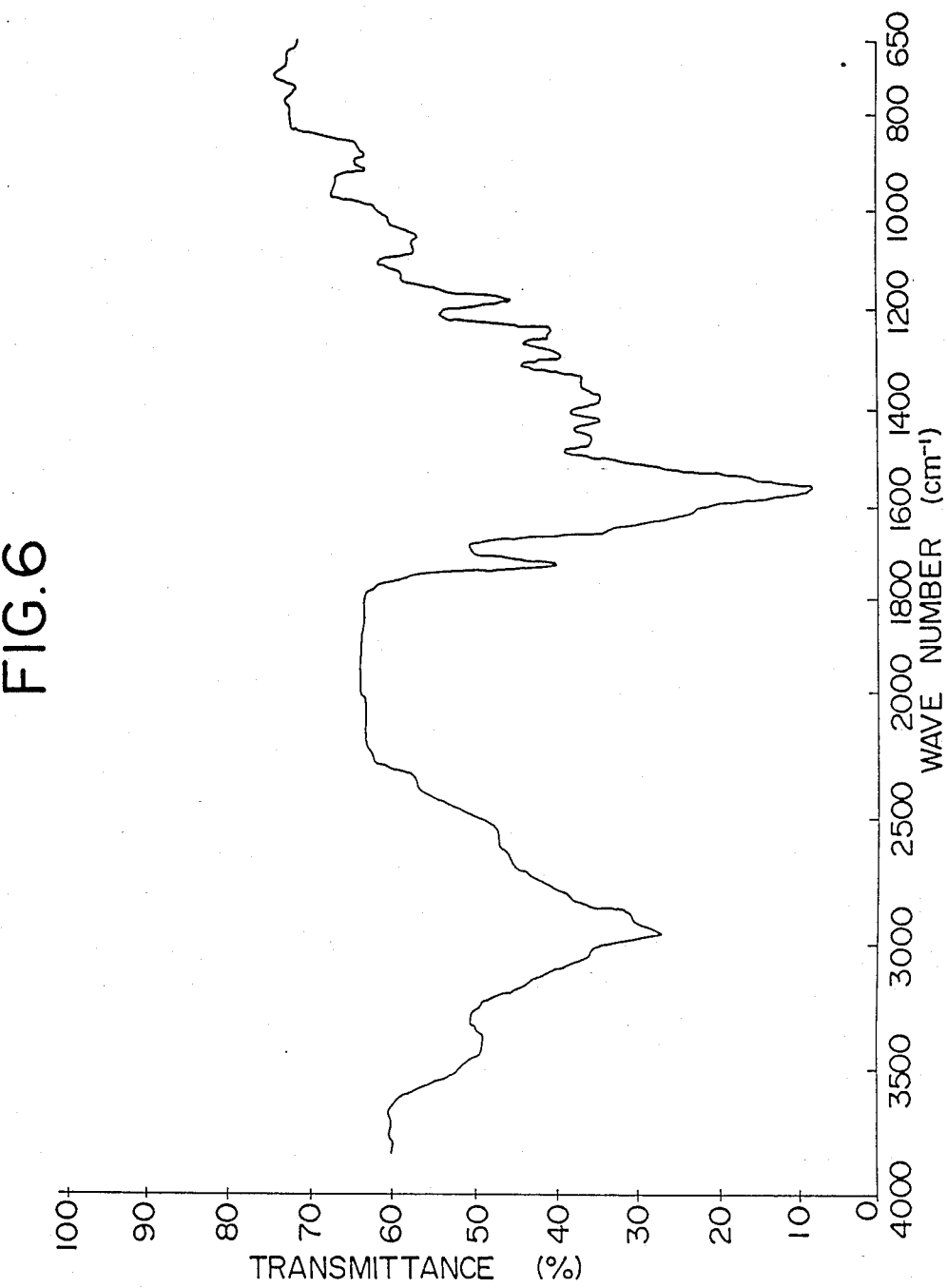

| Compound No. | $R^3$ | M | Physical Properties |
|---|---|---|---|
| 85 | " | $(HOC_2H_4)N^\oplus(CH_3)_3$ | $n_D^{20} = 1.5182$ refractive index |
| 86 | " | $H_2N^\oplus(C_2H_5)_2$ | $n_D^{20} = 1.5118$ refractive index |
| 87 | " | $H_2N^\oplus(C_2H_4OH)_2$ | $n_D^{20} = 1.5172$ refractive index |
| 88 | $C_2H_5$ | $H_3N^\oplus(n-C_3H_7)$ | $n_D^{20} = 1.5330$ (see FIG. 6) |
| 89 | " | $(C_2H_5)_2N^\oplus HCH_2\text{-}\langle\text{-}Cl\rangle$ | refractive index $n_D^{20} = 1.5392$ |
| 90 | " | $H_2N^\oplus(C_2H_4OH)_2$ | refractive index $n_D^{20} = 1.5283$ |
| 91 | " | $Na^\oplus$ | m.p. 225° C. (decomp.) |
| 92 | " | $K^\oplus$ | m.p. 200~205° C. |

TABLE 4

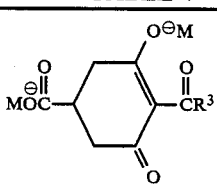

Figure 7:
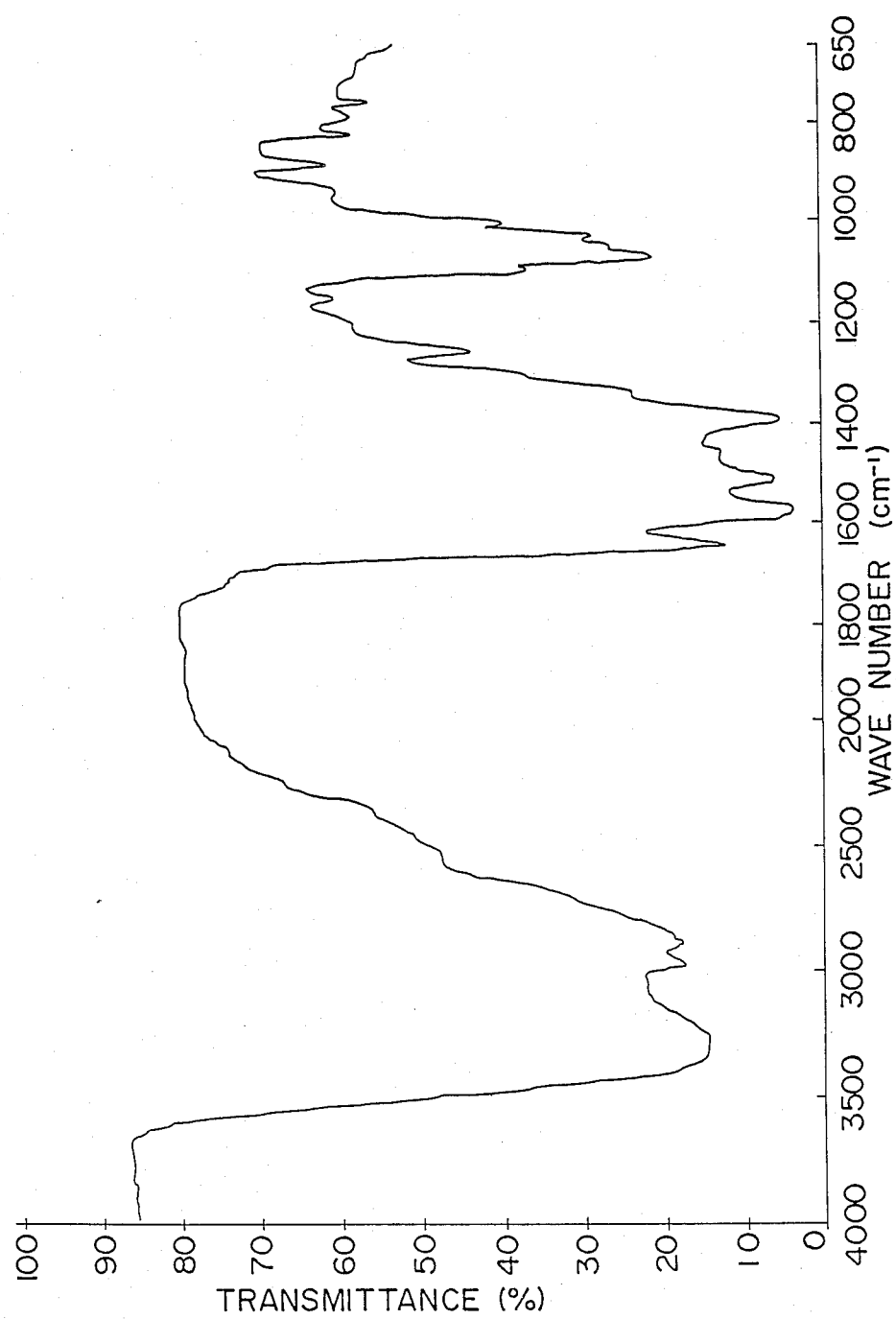

| Compound No. | $R^3$ | M | Physical Properties |
|---|---|---|---|
| 93 | $C_2H_5$ | $Na^\oplus$ | m.p. 240° C. (decomp.) |
| 94 | " | $H_2N^\oplus(C_2H_4OH)_2$ | refractive index $n_D^{20} = 1.5351$ (see FIG. 7) |
| 95 | $n\text{-}C_3H_7$ | $Na^\oplus$ | refractive index $n_D^{20} = 1.5261$ |

In the accompanying drawings, FIGS. 1, 2, 3, 4, 5, 6 and 7 show infrared absorption spectra of Compound Nos. 73, 74, 75, 78, 79, 88 and 94, listed in Tables 2–3, respectively.

Table 5 below shows the analytical results of nuclear magnetic resonance spectra (in CDCl$_3$) of some of the compounds according to the invention which are indicated with reference to Compound Number as shown in Tables 2–3.

TABLE 5

| Compound No. | Characteristic peaks for particular radicals in N.M.R. Spectra |
|---|---|
| 49 | $C\underline{H}_3CH_2OC(=O)\text{—}$: tri, 3H, 1.10 ppm |
|  | $CH_3C\underline{H}_2OC(=O)\text{—}$: q, 2H, 4.13 ppm |

TABLE 5-continued

| Compound No. | Characteristic peaks for particular radicals in N.M.R. Spectra |
|---|---|
|  | $\text{—}CC\underline{H}_3(=O)$: s, 3H, 2.33 ppm |
|  | $H_2N^\oplus(C\underline{H}_2CH_2OH)_2$: m, 4H, 3.66 ppm |
|  | $\underline{H}_2N^\oplus(CH_2CH_2O\underline{H})_2$: s, 4H, 4.46 ppm |
|  | cyclohexenone structure with $O^\ominus H_2N^\oplus(C\underline{H}_2CH_2OH)_2$ : m, 9H, 2.50~3.06 ppm |
|  | $C\underline{H}_3CH_2OC(=O)\text{—}$, $H_2N^\oplus(CH_2C\underline{H}_3)_2$: tri, 9H, 1.23 ppm |
|  | $CH_3C\underline{H}_2OC(=O)\text{—}$: q, 2H, 4.13 ppm |
|  | $\text{—}CC\underline{H}_3(=O)$: s, 3H, 2.33 ppm |
|  | $H_2N^\oplus(C\underline{H}_2CH_3)_2$: q, 4H, 3.03 ppm |
|  | $\underline{H}_2N^\oplus(CH_2CH_3)_2$: s, 2H, 9.13 ppm |
|  | cyclohexenone structure with $O^\ominus$ : m, 5H, 2.52~2.82 ppm |

TABLE 5-continued

| Compound No. | Characteristic peaks for particular radicals in N.M.R. Spectra |
|---|---|
| 51 | $\underline{C}H_3CH_2O\overset{O}{\underset{\|}{C}}-$, $-\overset{O}{\underset{\|}{C}}CH_2\underline{C}H_3$, $H_2N^{\oplus}(CH_2\underline{C}H_3)_2$: m, 12H, 0.89~1.39 ppm<br><br>$CH_3\underline{C}H_2O\overset{O}{\underset{\|}{C}}-$: q, 2H, 4.15 ppm<br><br>$\underline{H}_2N^{\oplus}(CH_2CH_3)_2$: s, 2H, 8.97 ppm<br><br>[cyclohexene structure with $O^{\ominus}H_2N^{\oplus}(\underline{C}H_2CH_3)_2$ and $-CO\underline{C}H_2CH_3$]: m, 11H, 2.52~3.16 ppm |
| 54 | $\underline{C}H_3CH_2O\overset{O}{\underset{\|}{C}}-$: tri, 3H, 1.24 ppm<br><br>$CH_3\underline{C}H_2O\overset{O}{\underset{\|}{C}}-$: q, 2H, 4.18 ppm<br><br>$H_2N^{\oplus}(CH_2\underline{C}H_2OH)_2$: m, 4H, 3.69 ppm<br><br>$H_2N^{\oplus}(CH_2CH_2\underline{O}H)_2$: s, 4H, 6.36 ppm<br><br>$-\overset{O}{\underset{\|}{C}}CH_2\underline{C}H_3$: tri, 3H, 1.09 ppm<br><br>[cyclohexene structure with $O^{\ominus}H_2N^{\oplus}(\underline{C}H_2CH_2OH)_2$ and $-CO\underline{C}H_2CH_3$]: m, 11H, 2.51~3.18 ppm |
| 56 | $\underline{C}H_3CH_2O\overset{O}{\underset{\|}{C}}-$: t, 3H, 1.23 ppm<br><br>$CH_3\underline{C}H_2O\overset{O}{\underset{\|}{C}}-$: q, 2H, 4.13 ppm<br><br>$-\overset{O}{\underset{\|}{C}}CH_2\underline{C}H_3$: t, 3H, 1.10 ppm<br><br>$\underline{H}_2N^{\oplus}-$: s, 2H, 10.0 ppm<br><br>$H_2N^{\oplus}(CH_2\underline{C}H=\underline{C}H_2)_2$: m, 6H, 5.00~6.16 ppm<br><br>$H_2N^{\oplus}(\underline{C}H_2CH=CH_2)_2$: d, 4H, 3.26 ppm<br><br>[cyclohexene structure with $O^{\ominus}$ and $-CO\underline{C}H_2CH_3CH_2CH_3$]: m, 7H, 2.69~3.17 ppm |
| 58 | $\underline{C}H_3CH_2O\overset{O}{\underset{\|}{C}}-$: t, 3H, 1.26 ppm<br><br>$CH_3\underline{C}H_2O\overset{O}{\underset{\|}{C}}-$: q, 2H, 4.16 ppm<br><br>$-\overset{O}{\underset{\|}{C}}CH_2\underline{C}H_3$: t, 3H, 1.08 ppm<br><br>$H_2N^{\oplus}(CH_2CH\overset{\underline{C}H_3}{\underset{\underline{C}H_3}{\diagdown}})_2$: d, 12H, 0.93 ppm<br><br>[cyclohexene structure with $O^{\ominus}H_2N^{\oplus}(\underline{C}H_2CH(CH_3)_2)_2$ and $-\overset{O}{\underset{\|}{C}}\underline{C}H_2CH_3$]: m, 11H, 2.52~3.20 ppm<br><br>$\underline{H}_2N^{\oplus}-$: s, 2H, 8.16 ppm<br><br>$H_2N^{\oplus}(CH_2\underline{C}H(CH_3)_2)_2$: m, 2H, 1.89 ppm |

Amongst the particular compounds of Tables 2-4, the following compounds are preferred in this invention.

(12) Compound No.54: [Bis-(2-hydroxyethyl)]ammonium salt of ethyl 3,5-dioxo-4-propionylcyclohexane-carboxylate.

(13) Compound No.74: Sodium salt of ethyl 3,5-dioxo-4-propionylcyclohexanecarboxylate.

(14) Compound No.93: Di-sodium salt of 3,5-dioxo-4-propionylcyclohexanecarboxylic acid.

(15) Compound No.94: Bis-{[bis-(2-hydroxyethyl)-]ammonium} salt of 3,5-dioxo-4-propionylcyclohexanecarboxylic acid.

(16) Compound No.55: [Bis-(2-hydroxypropyl)]ammonium salt of ethyl 3,5-dioxo-4-propionylcyclohexanecarboxylate.

The compounds of the general formula (I) can be prepared by a method briefly depicted according to the following reaction equations:

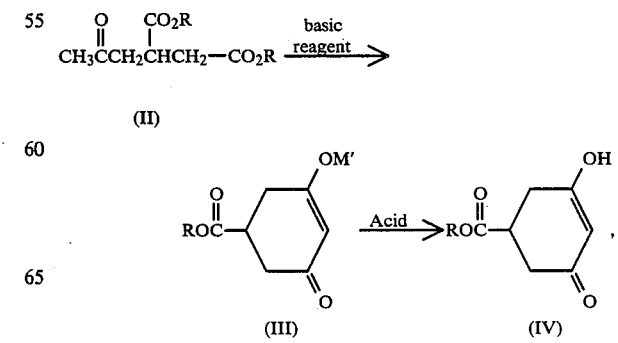

-continued

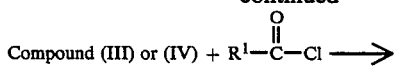

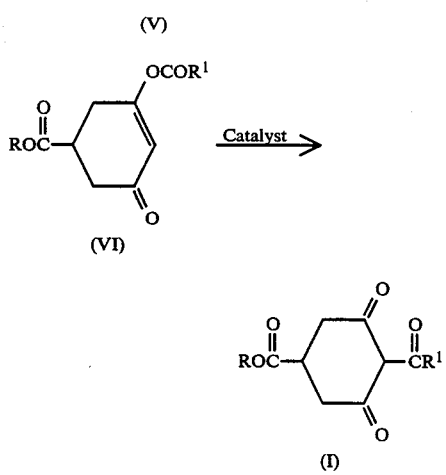

wherein R and R¹ are as defined hereinabove for the general formula (I) and M' is an alkali metal.

The 3,5-dioxo-cyclohexanecarboxylic acid alkyl ester alkali metal salt of the above formula (III) may be prepared by reacting an acetonylsuccinic acid di-alkyl ester compound of the formula (II) with a basic reagent in a suitable solvent. This cyclization reaction can be carried out at a temperature ranging from room temperature to the boiling point of the solvent used for a period of 1 to 10 hours. The basic reagent to be used in this reaction includes an alkali metal alcoholate such as sodium methylate, sodium ethylate and potassium tert-buthoxide or an alkali metal hydride such as sodium hydride. Examples of the solvent used here may be methanol, ethanol, benzene, toluene, xylene, N,N-dimethylformamide, dimethylsulfoxide and dimethylcellosolve.

The 3,5-dioxo-cyclohexanecarboxylic acid or its alkyl ester compound of the formula (IV) can be made by treatment of the compound (III) prepared as above with an acid such as hydrochloric acid.

The compound of the above formula (VI) can be prepared by condensing the compound (III) or (IV) in an inert organic solvent with an organic acid chloride of the formula (V) where R¹ is as defined hereinbefore, in the presence or absence of γ-picoline and in the presence or absence of a base. This condensation reaction may be carried out at a temperature in the range from −20° C. to the boiling point of the solvent when used, and preferably at or below ambient temperature. The reaction time may vary from 10 minutes to 7 hours depending upon the reaction conditions employed. The base which may optionally be used in this reaction includes any of such acid-binding agents which are generally employed for the conventional dehydrohalogenation, for examples, organic bases such as trimethylamine, triethylamine, diethylamine, dimethylamine or pyridine and inorganic bases such as sodium or potassium hydroxide. The solvent available for this reaction may include water and/or organic solvents such as toluene, benzene, xylene, dichloromethane, 1,2-dichloroethane, chloroform, carbon tetrachloride, N,N-dimethylformamide, dimethylsulfoxide and methylcellosolve. This condensation reaction is conveniently performed with the aid of γ-picoline which will act as phase transition catalyst when using water and organic solvent as the reaction medium.

The new compound of the formula (I) according to this invention can be produced by subjecting the intermediate compound of the above formula (VI) to a rearrangement reaction in the presence of a catalyst and an organic solvent at a temperature from room temperature to the boiling point of the solvent for a period of 1 to 10 hours. The catalyst to be used for this rearrangement reaction includes pyridine derivatives such as 4-N,N-dimethylaminopyridine, 4-N,N-diethylaminopyridine and 4-pyrolidinoaminopyridine; or N-alkylimidazole derivatives such as N-methylimidazole and N-ethylimidazole.

The new compound (I) of this invention can be prepared without isolation or purification of said intermediate compounds (III), (IV) and (VI).

According to a second aspect of this invention, therefore, there is provided a process for the production of a cyclohexane compound of the general formula (I):

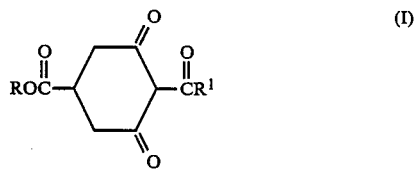

wherein R represents a hydrogen atom or an alkyl group, an alkylthioalkyl group or an unsubstituted or substituted phenyl group; and R¹ represents an alkyl group, an unsubstituted or substituted benzyl group, a phenethyl group, a phenoxymethyl group, a 2-thienylmethyl group, an alkoxymethyl group or an alkylthiomethyl group, or a salt of said cyclohexane compound, which comprises the steps of (a) reacting a compound of the formula (III):

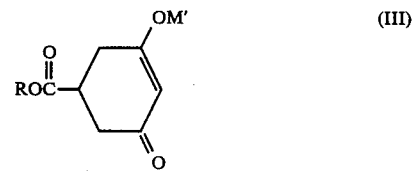

or a compound of the formula (IV):

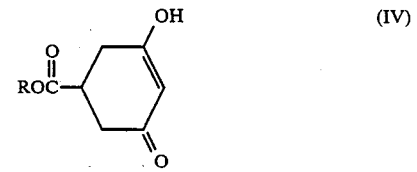

wherein R is as defined above and M' is an alkali metal atom, with an organic acid chloride compound of the formula (V):

wherein R¹ is as defined above, in an organic solvent and/or water as the reaction medium in the presence or absence of a base as an acid-binding agent to produce the compound of the formula (VI):

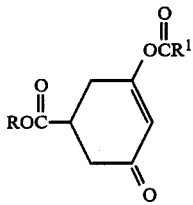

(VI)

wherein R and R¹ are as defined above, (b) subjecting the compound of the formula (VI) to an intermolecular rearrangement in the presence of a catalyst which is chosen from 4-N,N-dimethylaminopyridine, 4-N,N-diethylaminopyridine, 4-pyrolidinoaminopyridine, N-methylimidazole and N-ethylimidazole to produce the compound of the formula (I):

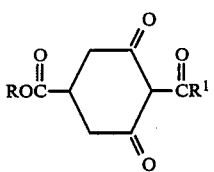

(I)

wherein R and R¹ are as defined above, and (c) if desired, reacting the compound of the formula (I) with an inorganic or organic cation to produce the salt of the compound (I) with said inorganic or organic cation.

As an alternative, such new compounds of the formula (I) where R is an alkyl group may be prepared by esterification of the corresponding free carboxylic acid compound according to the following briefed reaction scheme:

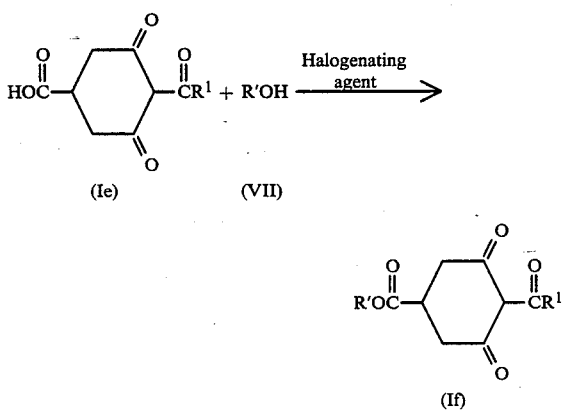

wherein R' represents an alkyl group and R¹ is as defined hereinbefore in the formula (I).

Thus, the compound of the formula (If) can be produced by a method comprising the reaction of the compound of the formula (Ie) with a halogenating agent in the presence or absence of a solvent and in the presence or absence of a base as an acid-binding agent, followed by a further esterification reaction of the acid halide derivative as formed with an alkanol(R'OH)of the formula(VII) in the presence or absence of a base. The reaction with the halogenating agent may be conducted at a temperature ranging from −20° C. to the boiling point of the halogenating agent or of the solvent when used, and preferably at a temperature of from −10° C. to 100° C. for a period of 10 minutes to 7 hours to give an acid halide derivative of the compound (Ie). The halogenating agent to be used for the above purpose may be thionyl chloride, phosphorus trichloride, phosphorus pentachloride and phosphorus oxychloride. As the solvent which may be used for the halogenation reaction, there may be mentioned dichloromethane, chloroform, carbon tetrachloride, benzene, toluene, xylene and the like.

The subsequent reaction of esterifying the acid halide derivative with the alkanol (VII) may be carried out at a temperature of −20° C. to 100° C. for a time of 10 minutes to 48 hours. The base which is conveniently used for the halogenation and esterification includes those which have generally been employed for the conventional dehydrohalogenation as the acid-binding agent in the art and may be selected from organic bases such as triethylamine, pyridine, N,N-dimethylaminopyridine and N,N-dimethylaniline; and inorganic bases such as sodium hydroxide, potassium carbonate and sodium bicarbonate. The esterification with the alkanol (VII) may be conducted after or without separation of the intermediate acid halide derivative from the reaction medium.

The salts of the new cyclohexane compounds of the formula (I) or (Ia) according to this invention can be prepared as follows:

Thus, for example, an organic or inorganic salt of the new cyclohexane compound may be produced by reacting in an organic solvent a compound of the general formula (I) or (Ia) with one or two or more equivalent proportions of a salt-forming reagent which is chosen from a primary, secondary or tertiary amine, a metal alcoholate, or a metal salt such as a chloride, sulfate, nitrate, acetate or carbonate; or hydride or hydroxide of a metal, for example, an alkali metal such as sodium, potassium; an alkaline earth metal such as calcium, magnesium, barium; aluminium, nickel, copper, manganese, cobalt, zinc, iron or silver. When the compound (I) or (Ia) is reacted with one equivalent proportion of the salt-forming reagent, either the salt formed will be in the form of the salt of the general formula (Ib) as indicated in Table 2 when the group R or R² in the compound of the formula (I) or (Ia) is alkyl, or the salt formed will be in the form of the salt of the general formula (Ic) as indicated in Table 3 when R or R² is hydrogen in the compound (I) or (Ia). If two or more equivalent proportions of the salt-forming reagent is reacted with the compound (I) or (Ia), the salt as formed will take the form of the general formula (Id) as indicated in Table 4, when R or R² is a hydrogen atom in the compound (I) or (Ia).

The new compounds of the formula (I) or (Ia) according to this invention may possibly undergo a tautomerism and may be present in the form of tautomeric isomers as shown below, which fall within the scope of this invention.

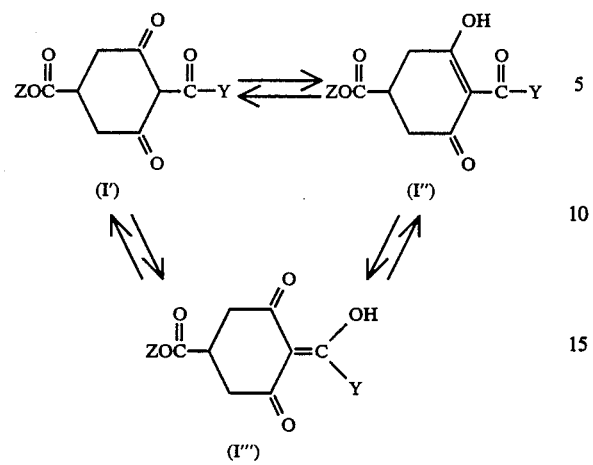

(I')  (I'')

(I''')

wherein Z denotes R or $R^2$ as defined hereinbefore and Y denotes $R^1$ or $R^3$ as defined hereinbefore.

Further, in an aqueous solution, the new compound salt of the formula (Ib) or (Ic) according to this invention may possibly change as shown below:

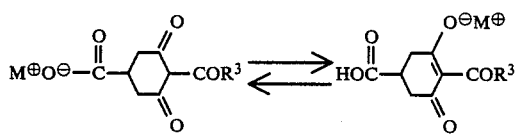

It may be added that when the cyclohexane compound of the formula (Ia) where $R^2$ is an alkyl group, is reacted with a primary, secondary or tertiary amine which may be represented by the formula

(VIII)

where $R^4$, $R^5$ and $R^6$ are each as defined hereinbefore but all of 0452 $R^4$, $R^5$ and $R^6$ cannot be each a hydrogen atom simultaneously, there is formed such salt of the compound (Ia) which may be deemed as the substituted ammonium salt of the formula

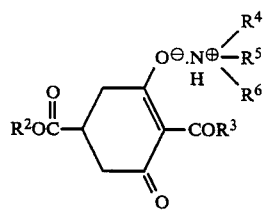

Further, when the cyclohexane compound of the formula (Ia) where $R^2$ is a hydrogen atom is reacted with a primary, secondary or tertiary amine of the formula (VIII), there is formed such salt of the compound (Ia) which may also be deemed as the substituted ammonium salt of the formula

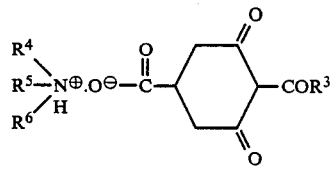

In Tables 2-4, the salts of the new compounds with amine are represented as the type of the substituted ammonium salt as shown just above.

The plant-growth regulating effects of the new compounds of the general formula (I) and the salts thereof are manifested predominantly as a stunting or dwarfing effect on the vegetative growth of plants, but other various plant-growth regulating effects may be manifested by modifying the nature of plants to be treated and the means, times and rates of application of the compounds or salts. Such plant-growth regulating effects which may be induced by the new compound of this invention include promotion of rooting, reduction in risk of lodging, promotion of sideshooting and root growth, maintenance of green color of stems and leaves, promotion or delay of flowering, promotion of fruiting and ripening, and increase in resistances to temperature hindrance, to phytotoxicity caused by herbicides and to fungal or bacterial diseases. These various effects are not always manifested at a time.

The new compounds (including the salts) of this invention can control internode elongation of cereals and prevent or reduce lodging of rice, wheat, barley, maise and the other crop-plants by foliage and/or soil-treatment. Application of the compound of this invention to seedlings of aquatic rice and growing vegetables can lead an improvement in quality, rooting after transplanting, and resistance to low temperature.

The foliage treatment with the new compound during the vegetative stage of crop plants, e.g. aquatic rice, wheat and barley also induces shortening of top leaves or improvement in leaf orientation and hence increases in light interception and utilization which will enhance the ripening and increase the overall grain yield of such crop-plants.

Moreover, the compound of this invention may suppress spindly growth of flowers, ornamental plants and horticultural plants which may be caused due to high temperature or sunshine shortage in plantation in a greenhouse.

The compound of the invention which exhibits the above-mentioned plant-growth regulating effects are very useful not only for agricultural and horticultural treatment but also for control of plant growth in non-crop lands. For instance, when the compound of this invention is applied onto lawns in park, playing field, golf link, airport or embankment or undergrowth grasses in orchard or pasture land, it is possible to inhibit the overluxuriant growth, to reduce the number of reaping and/or to facilitate the mowing operations as usually required for maintenance. Further, application of the new compound of this invention onto swards can promote sideshooting and increase the planting density of swards.

The compounds of this invention may be used as such for plant-growth regulating purposes but are more conveniently formulated into compositions for such usage. According to a third aspect of this invention, there is thus provided a plant-growth regulating composition comprising a compound of the general formula (I) as hereinbefore defined or a salt thereof in combination with a carrier or diluent.

The invention also provides a method of regulating the growth of plant, which comprises applying an effective amount of a cyclohexane compound of the formula (I) or a salt thereof of this invention to the foliage or seed of the plant to be treated or to the soil or locus where the plant to be treated is grown.

The compounds and salt can be applied in a number of ways, for example, they can be applied, formulated or unformulated, directly to the foliage of a plant, or they can be applied also to bushes and trees, to seeds or to other medium in which plants, bushes or trees are growing or are to be planted, or they can be sprayed on, dusted on or applied as a cream or paste formulation, or they can be applied as slow release granules.

The compounds are preferably used for agricultural and horticultural purposes in the form of a composition. The type of composition used in any instance will depend upon the particular purpose envisaged.

The compositions may be in the form of dusting powders or granules comprising the active ingredient and a solid diluent or carrier, for example fillers such as kaolin, bentonite, dolomite, calcium carbonate, talc, powdered magnesia, Fuller's earth, gypsum, diatomaceous earth and China clay.

The compositions may also be in the form of dispersible powders, granules or grains comprising a wetting agent to facilitate the dispersion in liquids of the powder or grains which may contain also fillers and suspending agents.

The aqueous dispersions or emulsions may be prepared by dissolving the active ingredient(s) in an organic solvent optionally containing wetting, dispersing or emulsifying agent(s) and then adding the mixture to water which may also contain wetting, dispersing or emulsifying agent(s). Suitable organic solvents are kerosene, cyclohexanone, methylethyl ketone, acetone, methanol and acetonitrile.

The compositions may also be in the form of liquid preparations for use as dips or sprays which are generally aqueous dispersions or emulsions containing the active ingredient in the presence of one or more of wetting agent(s), dispersing agent(s), emulsifying agent(s) or suspending agent(s). These agents can be anionic or nonionic agents.

The compositions for use as aqueous dispersions or emulsions are generally supplied in the form of a concentrate containing a high proportion of the active ingredient(s), and the concentrate is to be diluted with water before use.

The plant-growth regulating composition of this invention may usually be formulated into a wettable powder comprising 5 to 95%, preferably 10 to 50% by weight of the new compounds of this invention as active ingredient; 1 to 20%, preferably 5 to 10% by weight of surfactant; and 4 to 44%, preferably 40 to 85% by weight of solid carrier.

The composition of this invention may be formulated into an emulsifiable concentrate comprising 5 to 95%, preferably 20 to 70% by weight of the new compound of this invention as active ingredient; 1 to 40%, preferably 5 to 20% by weight of surfactant; and 4 to 94%, preferably 10 to 75% by weight of liquid carrier.

The composition of this invention may be made up as granules comprising 0.5 to 40%, preferably 2 to 10% by weight of the new compound of this invention as active ingredient; 1 to 20%, preferably 2 to 10% by weight of surfactant; and 40 to 98.5%, preferably 80 to 96% by weight of solid carrier. And, the composition of this invention may be formulated into dust comprising 0.5 to 10%, preferably 1 to 5% by weight of the active ingredient; and 99.5 to 90%, preferably 99 to 95% by weight of finely divided solid carrier.

The composition of this invention may also be formulated into a paste comprising 0.1 to 20%, preferably 1 to 10% by weight of the active ingredient, 1 to 20%, preferably 2 to 10% by weight of surfactant; and 60 to 98.9%, preferably 80 to 97% by weight of paste base.

The rate of application of the new compounds of this invention for use in the purposes of plant-growth regulation will normally depend on various factors, including nature of plants to be treated, application time and application means. In general, however, the rate of application may be in the range of 0.01 kg to 50 kg per hectare and preferably of 0.05 kg to 10 kg per hectare as the active ingredient.

For the purpose of preventing or reducing lodging of crop plants such as wheat, the rate of application may desirably be in a range of 0.1 kg to 1 kg per hectare as the active ingredient. For the purpose of suppressing the growth of swards in non-crop lands or undergrowth-grasses in orchards, the rate of application may be in a range of 0.5 kg to 5 kg per hectare as the active ingredient. For the purpose of regulating the growth of aquatic rice plants, the rate of application may be in the range of 0.5 kg to 5 kg per hectare as the active ingredient when it is applied to the soil, and the formulations to be applied to the foliage of aquatic rice plant may contain the active ingredient at a concentration of 100 ppm to 5000 ppm. In general, the composition of this invention may be formulated into a diluted or dilutable preparation containing the active ingredient at a concentration of 10 ppm to 10,000 ppm and preferably of 100 ppm to 5000 ppm for use in the foliage treatment.

This invention is now illustrated with reference to the following Examples to which this invention is not limited.

EXAMPLE 1

Preparation of Compound No. 15, namely ethyl 3,5-dioxo-4-butyrylcyclohexanecarboxylate.

To 150 ml of ethanol containing 3.4 g of sodium was added dropwise 31 g of diethyl acetonylsuccinate (or diethyl acetmethylsuccinate) over about one hour with stirring at ambient temperature. The mixture was heated under reflux for 2 hours and then cooled to room temperature, followed by distillation off of the ethanol under reduced pressure. There was thus obtained a brown viscous liquid comprising sodium salt of ethyl 3,5-dioxocyclohexanecarboxylate as formed, to which were added 100 ml of toluene, 50 ml of ice water and 0.3 g of γ-picoline and then added dropwise 15 g of n-butyryl chloride at ambient temperature under agitation over about 2 hours. The resultant reaction mixture was agitated for further 30 minutes and then the toluene layer was separated, washed with water, dried and admixed with 0.8 g of 4-N,N-dimethylaminopyridine. The admixture was heated with agitation at a temperature of 80°–90° C. for 3 hours. The toluene was then distilled off from the reaction solution under reduced pressure and the residue was chromatographed on a column of silica gel developed with benzene to give 19.5 g (55.9%) of the object compound (Compound No. 15).

Compound Nos. 1, 2 and Nos. 4–44 could be prepared by the same procedure as described in Example 1.

EXAMPLE 2

Preparation of Compound No. 26, namely ethyl 3,5-dioxo-4-n-valerylcyclohexanecarboxylate.

2.1 g of 5-ethoxycarbonyl-cyclohexane-1,3-dione, namely ethyl 3,5-dioxocyclohexanecarboxylate was dissolved in 20 ml of dichloromethane, to which was added 1.7 g of triethylamine and then added dropwise 1.9 g of n-valeryl chloride with stirring over 30 minutes. The mixture was continued to be stirred for 3 hours, and the reaction solution obtained was washed with water. The organic layer was separated from the aqueous phase, dried and concentrated to a small volume.

The concentrated solution was taken up in 20 ml of toluene, followed by addition of 0.6 g of 4-N,N-dimethylaminopyridine and heating at a temperature of 80°–90° C. for 4 to 5 hours. Subsequently, the toluene was removed from the reaction solution by distillation under reduced pressure, and the residue was chromatographed on silica gel using benzene as the developing solvent to yield 2.2 g (71.9%) of the aimed compound (Compound No. 26).

Compound Nos. 1–25 and Nos. 27–44 could be produced by the same procedure as stated in Example 2.

EXAMPLE 3

Preparation of Compound No. 51 (see Table 2)

1.0 g of ethyl 3,5-dioxo-4-propionylcyclohexanecarboxylate was dissolved in 20 ml of chloroform, to which was then added 1.0 g of diethylamine as the salt-forming reagent. The mixture was allowed to stand at room temperature for two hours, after which the chloroform and the excess of diethylamine were distilled off from the reaction solution under reduced pressure to yield 1.3 g of the object compound (Compound No. 51) as a pale brown solid and represented by the formula:

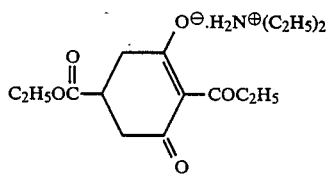

EXAMPLE 4

Preparation of Compound No. 54 (see Table 2)

4.0 g of ethyl 3,5-dioxo-4-propionylcyclohexanecarboxylate was dissolved in 50 ml of ethanol and 1.7 g of diethanolamine was added to the solution, followed by stirring for 30 minutes. The ethanol was then distilled off from the reaction solution under reduced pressure to precipitate a crystal, which was washed with ethyl ether and dried to afford 5.2 g of the object compound as a pale yellow crystal having a melting point of 76°–78° C.

EXAMPLE 5

Preparation of Compound No. 63

1.0 g of triethylamine was added to 1.0 g of ethyl 3,5-dioxo-4-propionylcyclohexanecarboxylate dissolved in 20 ml of chloroform, and the resultant mixture was allowed to stand at ambient temperature for 2 hours. The chloroform and the excess triethylamine were distilled off from the reaction solution under reduced pressure to yield 1.4 g of the desired compound (Compound No. 63) in the form of brown viscous liquid with a refractive index $n_D^{20} = 1.5098$.

EXAMPLE 6

Preparation of Compound No. 73

1.0 g of potassium salt of ethyl 3,5-dioxo-4-propionylcyclohexanecarboxylate was dissolved in water, to which was added 0.25 g of calcium chloride. The mixture was allowed to stand overnight to effect the cation-exchange reaction, after which the reaction solution was concentrated by evaporation of the water. The concentrated solution was extracted with hot ethanol and the ethanolic extract was admixed with hexane to precipitate a crystal. The latter was filtered and dried to give 0.7 g of the aimed compound as a colorless powder having a melting point of 213°–215° C.

EXAMPLE 7

Preparation of Compound No. 74

To 8.4 g of ethyl 3,5-dioxo-4-propionylcyclohexanecarboxylate dissolved in 80 ml of ethyl ether was added dropwise under agitation at room temperature 50 ml of ethanolic solution containing 1.4 g of sodium hydroxide. After completion of the addition, the precipitated crystal was collected by filtration and dried. Recrystallization from a mixed solvent of ethanol and hexane gave 7.2 g of the desired sodium salt compound as colorless needles with a melting point of 178.5°–179.5° C.

EXAMPLE 8

Preparation of Compound No. 78

2.0 g of ethyl 4-butyryl-5-dioxo-cyclohexanecarboxylate was added into ethanol containing 0.53 g of sodium ethylate, and the mixture was allowed to stand at room temperature for 3 hours. The ethanol was then distilled off from the reaction solution under reduced pressure to yield 2.17 g of the desired sodium salt as a pale yellow amorphous solid.

EXAMPLE 9

Preparation of Compound No. 84 (see Table 3)

1.3 g of 4-butyryl-3,5-dioxo-cyclohexanecarboxylic acid was dissolved in 20 ml of methanol and 0.58 g of triethylamine was added to the solution. The mixture was allowed to stand overnight at ambient temperature, after which the methanol was removed from the reaction solution by evaporation under reduced pressure to leave 1.8 g of the object compound (Compound No. 84) as a pale yellow viscous liquid with $n_D^{20} = 1.5182$.

The above procedure was repeated using choline in place of the triethylamine to give Compound No. 85.

EXAMPLE 10

Preparation of Compound No. 87

1.0 g of 4-butyryl-3,5-dioxo-cyclohexanecarboxylic acid was dissolved in 20 ml of methanol and 0.4 g of diethanolamine $(HOCH_2CH_2)_2NH$ was added to the solution. The mixture was allowed to stand at room temperature for 3 hours and the methanol was then removed from the reaction solution by evaporation under reduced pressure to give 1.4 g of the desired compound as a pale brown viscous liquid with $n_D^{20} = 1.5330$. This product was of the formula:

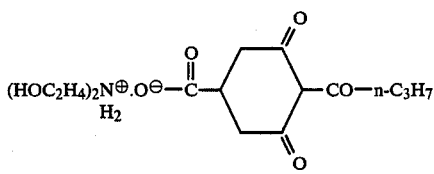

EXAMPLE 11

Preparation of Compound No. 91

0.84 g of sodium bicarbonate was added to 2.1 g of 3,5-dioxo-4-propionylcyclohexanecarboxylic acid dissolved in 30 ml of ethanol, and the mixture was heated under reflux for 3 hours. The reaction solution was then cooled and filtered to leave a crystal, which was recrystallized from ethanol to give 2.2 g of the desired compound as pale yellow flakes with a melting point of 225° C. (decomp.).

EXAMPLE 12

Preparation of Compound No. 93 (see Table 4)

1.4 g (6.6 m moles) of 3,5-dioxo-4-propionylcyclohexanecarboxylic acid was dissolved in 30 ml of ethanol, and 0.7 g (6.6 m moles) of anhydrous sodium carbonate was added to the solution. The resultant mixture was heated under reflux for 6 hours, after which the reaction solution was cooled and filtered to leave a crystal. Recrystallization of the crystal from a mixed solvent of ethanol, methanol and hexane gave 1.3 g of the desired di-sodium salt compound as a pale yellow powder having a melting point of 240° C. (decomp.).

EXAMPLE 13

Preparation of Compound No. 95

2.0 g of 4-butyryl-3,5-dioxo-cyclohexanecarboxylic acid was dissolved in a mixture of methanol and water (1:1), to which was then added 0.72 g of sodium hydroxide. After complete dissolution of the latter, the resulting solution was allowed to stand overnight, followed by removal of the methanol and water by distillation under reduced pressure. There was thus obtained 2.4 g of the object compound as a redish brown viscous liquid with $n_D^{20} = 1.5261$.

EXAMPLE 14

Preparation of ethyl 3,5-dioxo-4-propionylcyclohexanecarboxylate 4.2 g of ethyl 3,5-dioxocyclohexanecarboxylate and 3.4 g of triethylamine were dissolved in 50 ml of dichloromethane, to which was added dropwise 2.9 g of propionyl chloride under stirring at room temperature. The resultant mixture was allowed to react at ambient temperature for 2 hours, after which the reaction solution was washed with solution to remove the acidic matters from the reaction solution. The organic layer was then separated from the aqueous phase, dried and concentrated to a small volume. The concentrated solution was taken up in 20 ml of toluene, followed by addition of 0.5 g of 4-N,N-dimethylaminopyridine and heating the mixture at 85° C. for 3 hours. Thereafter, the toluene was removed from the reaction solution by distillation under reduced pressure, and the residue was chromatographed on silica gel using benzene as developing solvent to afford 2.5 g of the title compound (Compound No. 9 of Table 1) as colorless flakes having a melting point of 55°-56° C.

EXAMPLE 15

Preparation of ethyl 4-n-butyryl-3,5-dioxocyclohexanecarboxylate 28.8 g of sodium salt of ethyl 3,5-dioxocyclohexanecarboxylate was admixed with 100 ml of toluene and 50 ml of ice water, and to the resulting suspension was added 0.3 g of γ-picoline. To the mixture obtained was added dropwise 15 g of n-butyryl chloride with stirring over about two hours, and the resultant mixture was continued to be stirred for 30 minutes. The toluene layer was then separated from the aqueous phase, dried and concentrated to a small volume. The concentrated solution was dissolved in 20 ml of toluene and 0.8 g of 4-N,N-dimethylaminopyridine was added to the solution, which was then heated at 80°-90° C. under agitation for 3 hours. Thereafter, the toluene was removed from the reaction solution by distillation under reduced pressure, and the residue was chromatographed on silica gel developing with benzene to yield 19.5 g of the title compound (Compound No. 15 of Table 1) as pale yellow prisms with a melting point of 34°-35° C.

The following Examples 16–20 illustrate the preparation of the compositions according to this invention, in which parts are all by weight.

EXAMPLE 16

Wettable powder

A composition in the form of wettable powder was prepared by mixing homogeneously and grinding 10 parts of Compound No. 1, 85 parts of kieselguhr, 2 parts of sodium dinaphthylmethanesulfonate and 3 parts of sodium lignosulfonate.

A similar wettable powder was produced by the same procedure as above but using Compound No. 45 instead of Compound No. 1.

EXAMPLE 17

Emulsifiable concentrate

An emulsifiable concentrate was made up by mixing the ingredients, and stirring the mixture until all the constituents were dissolved.

| | |
|---|---|
| Compound No. 15 | 30 parts |
| Cyclohexane | 20 parts |
| Polyoxyethylenealkylaryl ether | 11 parts |
| Calcium alkylbenzenesulfonate | 4 parts |
| Methylnaphthalene | 35 parts |

A similar emulsifiable concentrate was prepared by the same procedure as described above but replacing Compound No. 15 by Compound No. 46.

EXAMPLE 18

Grains

A composition in the form of grains was prepared by uniformly mixing and grinding together 5 parts of Compound No. 13, 2 parts of sodium laurylsulfate, 5 parts of sodium lignosulfonate, 2 parts of carboxymethylcellulose and 86 parts of clay, followed by addition of 20 parts of water per 80 parts of the mixture. The resultant mixture was milled and formulated into grains of 14-32 mesh size by means of an extrusion granulator.

A similar granular composition was made up by repeating the above procedure but replacing Compound No. 13 by Compound No. 47.

EXAMPLE 19

Dusting powder 4 parts of Compound No. 16, 5 parts of kieselguhr and 91 parts of clay were homogeneously mixed and ground together to formulate into a dusting powder.

The above procedure was repeated using Compound No. 48 instead of Compound No. 16 to produce a similar dusting powder.

EXAMPLE 20

Paste formulation

A paste formulation was prepared by mixing uniformly parts of Compound No. 9, 1 part of xylene, 5 parts of polyoxyethylenesorbitan monolaurate and 89 parts of white vaseline as paste base.

A similar paste formulation was made up by the same procedure as mentioned above except that Compound No. 9 was replaced by Compound No. 49.

The following Examples illustrate the plant-growth regulating effects of the compounds according to this invention.

EXAMPLE 21

This Example illustrates the retardation effect of the compounds of this invention on the growth of aquatic rice plants.

Aquatic rice plants ("Kinmage" Variety) at the two-leaf stage were treated with the compounds of this invention under test. Thus, the compounds were formulated into a wettable powder as prepared in Example 16 and the wettable powder was diluted with such a volume of water that 1000 l of the diluted aqueous preparations as sprayed gave the rate of application of 1 kg of the active ingredient per hectare upon the foliage treatment by spraying.

On the day of the application and 3 weeks after the application of the compounds, the length of stems and leaves of the treated plants were measured, and retardation of growth was calculated by the following equation:

$$\text{Retardation (\%)} = \left(1 - \frac{B}{A}\right) \times 100$$

A = (Foliar length in untreated plots 3 weeks after application) − (Foliar length in untreated plots on the day of application)
B = (Foliar length in treated plots 3 weeks after application) − (Foliar length in treated plots on the day of application) The test results are set out in Table 6 below.

TABLE 6

| Compound No. tested | Retardation (%) | Compound No. tested | Retardation (%) |
|---|---|---|---|
| 1 | 57 | 24 | 63 |
| 2 | 58 | 25 | 81 |
| 3 | 57 | 26 | 55 |
| 4 | 64 | 27 | 56 |
| 5 | 67 | 28 | 49 |
| 6 | 52 | 29 | 41 |

TABLE 6-continued

| Compound No. tested | Retardation (%) | Compound No. tested | Retardation (%) |
|---|---|---|---|
| 7 | 49 | 30 | 30 |
| 8 | 67 | 31 | 22 |
| 9 | 71 | 32 | 61 |
| 10 | 78 | 33 | 63 |
| 11 | 65 | 34 | 58 |
| 12 | 74 | 35 | 57 |
| 13 | 68 | 36 | 76 |
| 14 | 59 | 37 | 74 |
| 15 | 82 | 38 | 62 |
| 16 | 79 | 39 | 61 |
| 17 | 56 | 40 | 53 |
| 18 | 58 | 41 | 54 |
| 19 | 66 | 42 | 58 |
| 20 | 69 | 43 | 57 |
| 21 | 77 | 44 | 61 |
| 22 | 63 | 45 | 53 |
| 23 | 62 | 46 | 63 |
| 47 | 65 | 73 | 66 |
| 48 | 52 | 74 | 72 |
| 49 | 46 | 75 | 70 |
| 50 | 44 | 76 | 62 |
| 51 | 61 | 77 | 65 |
| 52 | 60 | 78 | 59 |
| 53 | 62 | 79 | 63 |
| 54 | 64 | 80 | 57 |
| 55 | 63 | 81 | 72 |
| 56 | 60 | 82 | 69 |
| 57 | 62 | 83 | 66 |
| 58 | 59 | 84 | 70 |
| 59 | 65 | 85 | 49 |
| 60 | 64 | 86 | 58 |
| 61 | 65 | 87 | 58 |
| 62 | 60 | 88 | 61 |
| 63 | 57 | 89 | 68 |
| 64 | 60 | 90 | 57 |
| 65 | 65 | 91 | 73 |
| 66 | 63 | 92 | 70 |
| 67 | 62 | 93 | 65 |
| 68 | 70 | 94 | 71 |
| 69 | 66 | 95 | 67 |
| 70 | 67 | CCC (Comparative) | 0 |
| 71 | 64 | B-Nine (Comparative) | 0 |
| 72 | 71 | MH (Comparative) | 41 |

The results of Table 6 indicate that rice plant height can be controlled by the application of the new compounds of this invention and thus spindly growth of rice plant can be prevented.

EXAMPLE 22

This Example illustrates the stunting effect of the compounds of this invention on the growth of grass swards.

Creeping bentgrass (*Agrostis stolonifera*) ("Seaside" Variety) and Japanese lowngrass (*Zoysia japonica*) of 2 cm in height were sprayed with the diluted aqueous preparations containing the compounds of this invention. The diluted aqueous preparations as used were prepared by formulating the compounds into wettable powder as in Example 16 and diluting the wettable powder with such a volume of water that 1000 l of the diluted aqueous preparations as sprayed gave the rate of application of 1 kg of the active ingredient per hectare upon the foliage treatment by spraying.

5 Weeks after application of the compounds, assessment was made and percentage of retradation was calculated in the same way as described in Example 21. Phytotoxicity was also assessed for some of the test compounds and indicated by the following scales:

| Scales | Degree of Phytotoxicity |
| --- | --- |
| − | Not detected |
| ± | Small |
| + | Middle |
| ++ | Great |
| +++ | Kill |

The test results are shown in Tables 7a and 7b below.

TABLE 7a

| Compound | Retardation (%) | |
| --- | --- | --- |
| No. tested | Creeping bentgrass | Japanese lowngrass |
| 1 | — | 38 |
| 9 | 65 | 65 |
| 13 | 70 | 71 |
| 15 | 62 | 63 |
| 16 | — | 42 |
| 17 | — | 40 |
| 18 | — | 54 |
| 25 | 60 | 75 |

TABLE 7b

| Compound No. tested | Retardation (%) | | Phytotoxicity | |
| --- | --- | --- | --- | --- |
| | Creeping bentgrass | Japanese lowngrass | Creeping bentgrass | Japanese lowngrass |
| 46 | 45 | 68 | — | — |
| 54 | 51 | 58 | — | — |
| 74 | 53 | 59 | — | — |
| 90 | 49 | 54 | — | — |
| 94 | 40 | 43 | — | — |
| MH (Comparative) | — | 37 | ++ | + |

From the results of Tables 7a and 7b as above, it will be seen that the new compounds and salts of this invention exert the stunting or dwarfing effects on lawn grasses for a long period without significant phytotoxic effects and without deteriously affecting the appearance (particularly the color) of the grass, so that the compounds of this invention are useful to reduce the need for mowing the grass swards.

EXAMPLE 23

This Example illustrates the improvements in quality of rice seedlings by application of the compounds of this invention.

Emergent seeds of aquatic rice ("Kinmaze" Variety) were sown in a rice-planting case of 30×60 cm in size, then covered with soil and irrigated with water. The compounds under test were formulated into an emulsifiable concentrate as stated in Example 17 which was then diluted with water so that the diluted emulsions contained the active ingredient at the concentrations as indicated in Table 8 below. The diluted emulsions so formulated were sprayed onto the soil surface at the rate of 20 ml per case. The cases were then kept in a thermostatic chamber at 30° C. for 3 days and further placed in a greenhouse. When the rice seedlings in untreated plots had reached the stage of 2.5 leaf age, the height of seedlings, leaf age and dry weights of the foliage parts (stems/leaves) and roots of the treated and untreated plants were measured. Some members of the seedlings were washed with water, and then the seedlings were transplanted into and placed at an angle of 45° in a pot flooded with water to 2 cm depth, after cutting the roots into the constant length of 2 cm. 10 Days later, the rising angle of the seedlings and the chlorophyll content of their second leaf were determined.

The results are shown in Table 8 below, where the assessment particulars other than the rising angle are indicated in terms of the percentages based on the results obtained for the untreated plots.

It will be seen from Table 8 that the compounds of this invention can suppress the excessive growth of rice seedlings in a planting case, promote the growth of roots and accelerate the rooting of transplanted rice seedlings.

TABLE 8

| Compound No. tested | Concentration (ppm) of active ingredient in the sprayed emulsion | Quality of rice seedling at the time transplantation | | | | Quality of rice seedling 10 days after transplantation | |
| --- | --- | --- | --- | --- | --- | --- | --- |
| | | Plant height (%) | Leaf age (%) | Dry weight of foliage parts (%) | Dry weight of root parts (%) | Raising angle of seedling (degree) | Chlorophyll content of second leaf % |
| 15 | 4000 | 59 | 100 | 92 | 113 | 90 | 111 |
| | 2000 | 67 | 100 | 97 | 119 | 90 | 110 |
| | 1000 | 88 | 100 | 101 | 120 | 87 | 108 |
| 54 | 1000 | 83 | 104 | 98 | 110 | 90 | 113 |
| 55 | 1000 | 80 | 108 | 96 | 115 | 90 | 120 |
| 57 | 1000 | 85 | 104 | 98 | 112 | 90 | 112 |
| 70 | 1000 | 79 | 108 | 96 | 119 | 90 | 136 |
| 87 | 1000 | 76 | 108 | 94 | 119 | 90 | 139 |
| 93 | 1000 | 83 | 104 | 97 | 112 | 90 | 118 |
| Untreated | — | 100 | 100 | 100 | 100 | 75 | 100 |

EXAMPLE 24

This Example illustrates the suppressive effect of the compounds of this invention on internode elongation of aquatic rice plants.

3 hills (each hill comprising two seedlings) of aquatic rice seedlings ("Kinmaze" Variety) at the 3 leaf stage were transplanted in a 1/2000 are Wagner pot. 35 Days after transplanting, a dilute aqueous emulsion containing the test compound which had been prepared by diluting with water an emulsifiable concentrate formulated as in Example 17 was added dropwise into the flooding water in the pot at an application rate of 1 kg of the active ingredient per hectare.

3 Months after the application, assessments were made on the stem length, length of each of the first to fifth internodes and weight of each unit internode. The test results are indicated in Table 9 in terms of the percentages based on those in the untreated plots. The "unit internode weight" means dry weight of the internode of 1 cm long.

TABLE 9

| Compound No. tested | Stem length | Each internode length | | | | | Unit internode weight | | | | |
|---|---|---|---|---|---|---|---|---|---|---|---|
| | | First | Second | Third | Fourth | Fifth | First | Second | Third | Fourth | Fifth |
| 15 | 87 | 98 | 91 | 63 | 68 | 59 | 106 | 108 | 114 | 120 | 123 |

From the results of Table 9 as above, it will be seen that the new compounds of this invention exert the stunting effects on the elongation of the lower (third to fifth) internodes of aquatic rice plants and make these lower internodes thick and strong, so that the compounds are useful to reduce the risk of lodging of aquatic rice plants.

EXAMPLE 25

This Example illustrates that the compounds of this invention reduce the risk of lodging of wheat plants.

Seeds of wheat ("Norin" No. 61 Variety) were sown in a field. When the wheat plants were grown to a stage of 30 to 40 cm in height, the field was divided into several plots each of 10 m² area The wheat plants in each plot were treated by spraying their foliage evenly with a diluted aqueous preparations which had been prepared by formulating the compounds of this invention into a wettable powder as stated in Example 16and diluting the wettable powder with such a volume of water that 500 liters of the diluted aqueous preparations so sprayed gave the rates of application of active ingredient as indicated in the following Table 10. For comparison purpose, 2-chloroethyl trimethyl ammonium chloride (CCC, known as chlormequat) was tested in the same manner as above.

80 Days after the treatment, the length of stem of the wheat plants and the extent of lodging were evaluated. The results obtained are tabulated in Table 10 below.

TABLE 10

| Compound No. tested | Rate of application of active ingredient (kg per hectare) | Stem length (%) | Extent of lodging |
|---|---|---|---|
| 9 | 0.2 | 83 | Very slight |
| | 0.4 | 76 | None |
| 15 | 0.2 | 80 | Very slight |
| | 0.4 | 75 | None |
| 25 | 0.2 | 83 | Very slight |
| | 0.4 | 77 | None |
| 37 | 0.2 | 85 | Slight |
| | 0.4 | 80 | Very slight |
| | 0.5 | 101 | None |
| CCC (comparative) | 1.0 | 81 | Slight |
| | 2.0 | 77 | Very slight |
| Untreated | — | 100 | Medium to great |

EXAMPLE 26

This Example demonstrates that the salts of the cyclohexane compounds of the formula (Ia) according to this invention have reduced influences on eyes in contact with the latter.

3 Rabbits (Female, "Japan White" Variety, 4 months-age) of which eyeballs were found to suffer from no damage by a check with 5% aqueous fluorescein sodium solution were fixed on a fixing table. 100 mg of the test compounds as such were dropped into the left eyes of the rabbits and their eyelids were closed for one seconds, after which the rabbits were placed in a breeding case. The right eyes were remaining untreated for control. Eye-examinations were made 24 hours and 2, 3, 4, 7, 14 and 21 days after the treatment. The stimulus responses were evaluated in respect of various observations as indicated in Table 11, and the results are set out in Table 12.

TABLE 11

| Cornea | | |
|---|---|---|
| (A) | Opacity-Turbidity (the most opaque region of cornea was examined) were estimated by the following scales: | |
| | Scale 1 | Sporadical or diffusive opacity occurred to such extent that iris still remained clearly visible. |
| | Scale 2 | Opacity occurred to such extent that fine Parts of iris were somewhat dimly visible. |
| | Scale 3 | Opacity occurred to such extent that fine parts of iris were indistinct and the size of pupil is visually distinguishable with difficulty. |
| | Scale 4 | Opacity occurred to such extent that iris was not visible. |
| (B) | Area suffering from corneal damaqe (denoted as "Area" below) was scaled as follows: | |
| | Scale 1 | $0 <$ "Area" $< \frac{1}{4}$ |
| | Scale 2 | $\frac{1}{4} \leq$ "Area" $< \frac{1}{2}$ |
| | Scale 3 | $\frac{1}{2} \leq$ "Area" $< \frac{3}{4}$ |
| | Scale 4 | $\frac{3}{4} \leq$ "Area" |

A value of a product of scale (A)×scale (B)×5 was calculated and indicated as "Evaluation scores" of stimulus to cornea in the following Table 12, but this calculated value did not extend over the maximum value 80 even for the worst case.

| Iris | | |
|---|---|---|
| (A) | Scale 1 | one or more signs of acceleration of wrinkle formation, hyperemia, swelling and hyperemia of corneal surroundings in iris were detectable but reflection response of iris to light was still good. |
| | Scale 2 | one or more signs of no reflection response of iris to light, bleeding and wide-spread breakdown were detectable. |

A value of a product of scale (A)×5 was calculated and indicated as "Evaluation scores" of stimulus to iris in Table 12, but this calculated value did not extend over the maximum value 10 even for the worst case.

| Conjunctiva | | |
|---|---|---|
| (A) | Redness (only the redness developed in the eyelid conjunctiva was examined.) | |
| | Scale 1 | Acceleration of hyperemia was observed. |
| | Scale 2 | Wide-spread, deep-color redness and difficulty in identification of vasa were observed. |
| | Scale 3 | Wholly-spread, deep-color redness was observed |
| (B) | Chemosis | |
| | Scale 1 | Acceleration of chemosis (including nictitating membrane) was observed. |
| | Scale 2 | Swelling associated with partial valgum of eyelid was observed. |
| | Scale 3 | Eyelid closing (in about half region) associated with swelling was observed. |
| | Scale 4 | Eyelid closing (about half to whole region) with swelling was observed. |
| (C) | Secreta | |

-continued

| Conjunctiva | |
|---|---|
| Scale 1 | More than ordinary amount (excluding the small quantity of secreta usually observed in inner canthus of heathy animal) of secreta was observed. |
| Scale 2 | Secreta was formed in the amount to wet and stain eyelid and also hairs contact with eyelid |
| Scale 3 | Secreta was formed in the amount to wet and stain eyelid and also the eye surroundings over a fairly wide region. |

A value of a product of [scale (A)+scale (B)+scale (C)]×2 was calculated and indicated as "Evaluation scores" in term of secreta in Table 12, but this calculated value did not extend over the maximum value 20 for the worst case.

TABLE 12

| Compound No. tested | Compound No. 54 | Compound No. 74 | Compound No. 93 | Compound No. 94 | Compound No. 9 (comparative) |
|---|---|---|---|---|---|
| | Evaluation scores of stimulus | | | | |
| Cornea | | | | | |
| Body Weight (kg) | 2.5 2.6 2.5 | 2.7 3.0 2.7 | 3.0 2.6 2.5 | 2.5 2.5 2.1 | 2.7 2.6 2.6 |
| 24 hours | 0 0 0 | 0 5 0 | 0 0 0 | 0 0 0 | 20 15 20 |
| 2 days | 0 0 0 | 0 0 0 | 0 0 0 | 0 0 0 | 20 15 20 |
| 3 days | 0 0 0 | 0 0 0 | 0 0 0 | 0 0 0 | 20 10 15 |
| 4 days | 0 0 0 | 0 0 0 | 0 0 0 | 0 0 0 | 20 10 20 |
| 7 days | 0 0 0 | 0 0 0 | 0 0 0 | 0 0 0 | 20 5 5 |
| 14 days | 0 0 0 | 0 0 0 | 0 0 0 | 0 0 0 | 5 0 0 |
| 21 days | 0 0 0 | 0 0 0 | 0 0 0 | 0 0 0 | 0 0 0 |
| Average | 0 | 0.2 | 0 | 0 | 11.4 |
| Iris | | | | | |
| 24 hours | 0 0 0 | 0 5 0 | 0 0 0 | 0 0 0 | 5 0 0 |
| 2 days | 0 0 0 | 0 0 0 | 0 0 0 | 0 0 0 | 5 0 0 |
| 3 days | 0 0 0 | 0 0 0 | 0 0 0 | 0 0 0 | 5 0 0 |
| 4 days | 0 0 0 | 0 0 0 | 0 0 0 | 0 0 0 | 0 0 0 |
| 7 days | 0 0 0 | 0 0 0 | 0 0 0 | 0 0 0 | 0 0 0 |
| 14 days | 0 0 0 | 0 0 0 | 0 0 0 | 0 0 0 | 0 0 0 |
| 21 days | 0 0 0 | 0 0 0 | 0 0 0 | 0 0 0 | 0 0 0 |
| Average | 0 | 0.2 | 0 | 0 | 0.7 |
| Conjunctiva | | | | | |
| 24 hours | 4 2 2 | 2 4 2 | 6 4 6 | 0 0 0 | 8 8 6 |
| 2 days | 0 0 0 | 0 0 0 | 0 0 0 | 0 0 0 | 6 4 4 |
| 3 days | 0 0 0 | 0 0 0 | 0 0 0 | 0 0 0 | 2 0 0 |
| 4 days | 0 0 0 | 0 0 0 | 0 0 0 | 0 0 0 | 2 0 0 |
| 7 days | 0 0 0 | 0 0 0 | 0 0 0 | 0 0 0 | 0 0 0 |
| 14 days | 0 0 0 | 0 0 0 | 0 0 0 | 0 0 0 | 0 0 0 |
| 21 days | 0 0 0 | 0 0 0 | 0 0 0 | 0 0 0 | 0 0 0 |
| Average | 0.4 | 0.4 | 0.8 | 0 | 1.9 |

What we claim is:

1. A process for the production of a cyclohexane compound represented by the general formula (I):

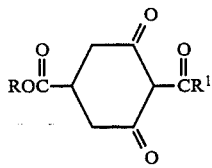  (I)

wherein R represents a hydrogen atom or an alkyl group, an alkylthioalkyl group or an unsubstituted or substituted phenyl group; and $R^1$ represents an alkyl group, an unsubstituted or substituted benzyl group, a phenethyl group, a phenoxymethyl group, a 2-thienylmethyl group, an alkoxymethyl group or an alkylthiomethyl group, or a salt of said cyclohexane compound (I) which comprises the steps of:

(i) reacting and cyclizing an acetonylsuccinic acid di-alkyl ester of the formula (II)

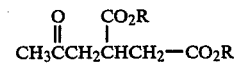  (II)

wherein R is as defined above, by reacting it with a basic agent selected from alkali metal alcoholates and alkali metal hydrides in an organic solvent at a temperature of from room temperature to the boiling point of the solvent used, to produce a 3,5-dioxo cyclohexane-carboxylic acid alkyl ester akali metal salt of the formula (III)

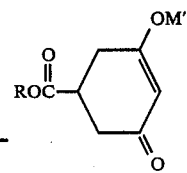  (III)

wherein R is as defined above and $M_i$ is the alkali metal, (ii) optionally treating the compound of the formula (III) with an acid to produce a 3,5-dioxo-cyclohexanecarboxylic acid or its alkyl ester compound of the formula (IV)

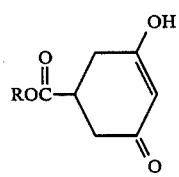  (IV)

wherein R is as defined above, (iii) reacting compound of the formula (III):

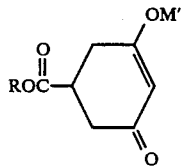

or a compound of the formula (IV):

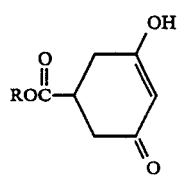

wherein $R^1$ is as defined above and $M'$ is an alkali metal atom, with an organic acid chloride compound of the formula (V):

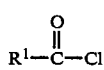

wherein $R^1$ is as defined above, in an organic solvent and water as the reaction medium wherein the organic solvent is selected from toluene, benzene, xylene, dichloromethane, 1,2-dichloroethane, chloroform and carbon tetrachloride in the presence of γ-picoline as a phase-transition catalyst and in the presence or absence of a base as an acid-binding agent at a temperature of from −20° C. to the boiling point of the solvent used, to produce the compound of the formula (VI):

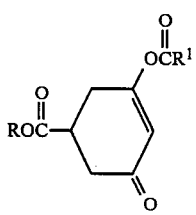

wherein R and $R^1$ are as defined above, (iv) subjecting the compound if the formula (VI) in an organic solvent to intramolecular rearrangement at a temperature of from room temperature to the boiling point of the solvent used, in the presence of a catalyst chosen from pyridine derivatives and N-alkylimidazole derivatives, to produce the compound of the formula (I):

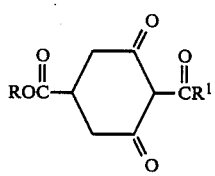

wherein R and $R^1$ are as defined above.

2. A process according to claim 1, in which the step of subjecting the compound (VI) to the intramolecular rearrangement to produce the compound (I) is carried out in the presence of a catalyst which is chosen from 4-N,N-dimethylaminopyridine, 4-N,N-diethylaminopyridine, 4-pyrolidinoaminopyridine, N-methylimidazole and N-ethylimidazole.

3. A process as claimed in claim 1, in which the process is conducted without effecting the isolation and purification of the intermediate products of formula (III), (IV) and (VI) as formed respectively in the steps (i), (ii) and (iii) of the process.

4. A process as claimed in claim 1, in which a compound of formula (II) where R is an alkyl group is cyclized in the step (i) of the process, and the compound of formula (III) or (IV) where R is the alkyl group is reacted with an organic acid chloride compound of formula (V) where $R^1$ is an alkyl group.

5. A process for the production of a 3,5-dioxocyclohexanecarboxylic acid compound having formula (I)

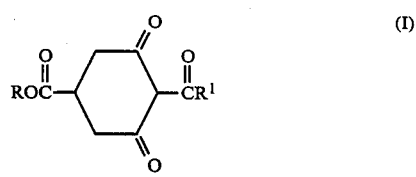

wherein R represents a hydrogen atom or an alkyl group, an alkylthioalkyl group or an unsubstituted or substituted phenyl group; and $R^1$ represents an alkyl group, an unsubstituted or substituted benzyl group, a phenethyl group, a phenoxymethyl group, a 2-thienylmethyl group, an alkoxymethyl group or an alkylthiomethyl group, or a salt of said cyclohexane compound (I) which comprises the consecutive steps of:

(a) heating a mixture of an acetonylsuccinic acid dialkyl ester of formula (II)

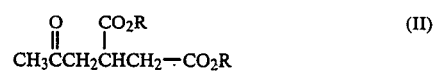

wherein R is as defined as above, an alkali metal ethylate or methylate, and ethanol or methanol to cyclize the compound of formula (II) and thereby produce a 3,5-dioxocyclohexanecarboxylic acid alkyl ester alkali metal salt of formula (III)

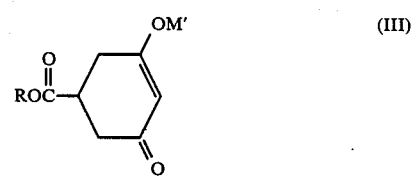

wherein R is as defined above and $M'$ represents an alkali metal, (b) distilling off the ethanol or methanol under reduced pressure from the reaction solution of the step (a) reaction, (c) admixing the resultant residue of the step (b) comprising the product of formula (III) produced, with toluene and water as well as γ-picoline and an organic acid chloride of formula (v)

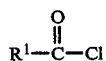

(V)

wherein $R^1$ is as defined above, (d) agitating the resulting mixtures of the step (c) to conduct the reaction between the compound of formula (III) and the chloride of formula (V), (e) separating the resulting reaction mixture containing the reaction product of formula (VI)

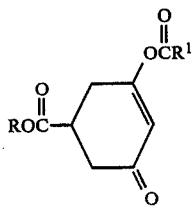

(VI)

wherein R and $R^1$ are defined above, into the aqueous phase and the toluene phase containing the reaction product compound (VI), (f) separating the toluene phase and washing the toluene phase with water and drying the water-washed toluene phase, (g) admixing the dried toluene phase with a catalyst selected from 4-N,N-dimethyl-aminopyridine, 4-N,N-diethylaminopyridine, 4-pyrolidinoaminopyridine, N-methylimidazole and N-ethylimidazole, and (h) heating under agitation the resultant organic solution of the step (g) containing the compound (VI) and said catalyst to conduct the intramolecular rearrangement of the compound of formula (VI) to produce the compound of the formula (I).

6. The process of claim 5, wherein the steps (a) to (h) of the process are carried out consecutively in a single reaction vessel without isolation and purification of the intermediate products of formula (III), (IV) and (VI) by such procedures.

* * * * *